United States Patent
Kahn

(10) Patent No.: US 7,563,825 B1
(45) Date of Patent: *Jul. 21, 2009

(54) MODULATION OF BETA-CATENIN COACTIVATOR INTERACTIONS TO EFFECT STEM CELL GROWTH OR DIFFERENTIATION

(75) Inventor: Michael Kahn, Kirkland, WA (US)

(73) Assignee: Choongwae Pharma Corporation, Seoul (KR)

(*) Notice: Subject to any disclaimer, the term of this patent is extended or adjusted under 35 U.S.C. 154(b) by 330 days.

This patent is subject to a terminal disclaimer.

(21) Appl. No.: 11/377,898

(22) Filed: Mar. 16, 2006

Related U.S. Application Data

(60) Provisional application No. 60/663,363, filed on Mar. 18, 2005.

(51) Int. Cl.
*A01N 25/00* (2006.01)
(52) U.S. Cl. ..................................... 514/789
(58) Field of Classification Search .............. 514/789.5, 514/789
See application file for complete search history.

(56) References Cited

U.S. PATENT DOCUMENTS 6,762,185 B1  7/2004  Kahn

OTHER PUBLICATIONS

Alonso, L. and Fuchs, E., Stem Cells of the Skin Epithelium, *Proc. Nat'l. Acad. Sci. USA 100*(Suppl. 1):11830-11835, Sep. 2003.
Emami, K. et al., A Small Molecule Inhibitor of β-Catenin/Cyclic AMP Response Element-Binding Protein Transcription, *Proc. Nat'l. Acad. Sci. USA*, 101(34):12682-12687, Aug. 2004.
Gat, V. et al., De Novo Hair Follicle Morphogenesis and Hair Tumors in Mice Expressing a Truncated β-Catenin in Skin, *Cell 95*:605-614, Nov. 1998.
Giles, R, et al., Caught Up in a Wnt Storm: Wnt Signaling in Cancer, *Biochim. Biophys. Acta 1653*(1):1-24, 2003.
Ilyas, M., Wnt Signalling and the Mechanistic Basis of Tumour Development, *J. Pathol. 205*:130-144, 2005.
Kim, P. et al., Surviving and Molecular Pathogenesis of Colorectal Cancer, *Lancet 362*:205-209, 2003.
Kolligs, F. et al., γ-Catenin is Regulated by the APC Tumor Suppressor and Its Oncogenic Activity is Distinct From That of β-Catenin, *Genes & Development 14*:1319-1331, 2000.
Rebel, V. et al., Distinct Roles for CREB-Binding Protein and p300 in Hematopoietic Stem Cell Self-Renewal, *PNAS 99*(23):14789-14794, Nov. 2002.
Reya, T., A Role for Wnt Signalling in Self-Renewal of Haematopoietic Stem Cells, *Nature 423*:409-414, May 2003.
Roth, J. et al., Differential Role of p300 and CBP Acetyltransferase During Myogenesis: p300 Acts Upstream of MyoD and Myf5, *EMBO 22*(19):5186-5196, 2003.
Ryo, A. et al., Pin1 Regulates Turnover and Subcellular Localization of β-Catenin By Inhibiting Its Interaction with APC, *Nature Cell Biology 3*:793-801, Sep. 2001.
Sato, M. et al., Maintenance of Pluripotency in Human and Mouse Embryonic Stem Cells Through Activation of Wnt Signaling by a Pharmacological GSK-3-Specific Inhibitor, *Nature Medicine 10*(1):55-63, Jan. 2004.
Song, X. and Xie, T., Wingless Signaling Regulates the Maintenance of Ovarian Somatic Stem Cells in Drosophila, *Development 130*:3259-3268, Apr. 2003.
Teo, J. et al., Specific Inhibition of CBP/β-Catenin Interaction Rescues Defects in Neuronal Differentiation Caused by a Presenilin-1 Mutation, *PNAS 102*(34):12171-12176, Aug. 2005.
Tetsu, O. and McCormick, F., β-Catenin Regulates Expression of Cyclin D1 in Colon Carcinoma Cells, *Nature 398*:422-426, Apr. 1999.
Walsh, J. and Andrews, P., Expression of Wnt and Notch Pathway Genes in a Pluripotent Human Embryonal Carcinoma Cell Line and Embryonic Stem Cells, *APMIS 111*:197-211, 2003.
Wodarz, A. and Nusse, R., Mechanisms of Wnt Signaling in Development, *Annu. Rev. Cell Dev. Biol. 14*:59-88, 1998.
Rebel, V. et al., Amplification of Sca-1$^+$ Lin$^-$ WGA$^+$ Cells in Serum-Free Cultures Containing Stell Factor, Interleukin-6, and Erythropoietin With Maintenance of Cells with Long-Term In Vivo Reconstituting Potential, *Blood 83*(1):128-136, 1994.
Rebel, V. and Landsdorp, P., Culture of Purified Stem Cells from Fetal Liver Results in Loss of In Vivo Repopulating Potential, *J. of Hematotherapy 5*(1):25-37, 1996.
Sherley, J., Asymmetric Cell Kinetics Genes: The Key to Expansion of Adult Stem Cells in Culture, *Stem Cells 20*:561-572, 2002.

*Primary Examiner*—Maryam Monshipouri
(74) *Attorney, Agent, or Firm*—Seed IP Law Group PLLC

(57) ABSTRACT

Methods and agents are disclosed for modulating the interaction of β-catenin or γ-catenin with CBP or p300. Agents that increase the binding of CBP to β-catenin are associated with enhancing the β-catenin-related proliferation of adult stem cells, including hematopoietic stem cells, neural stem cells, skin stem cells, and pancreatic stem cells.

8 Claims, 4 Drawing Sheets

Differentiation Medium　　　Growth Medium　　　Growth Medium +
　　　　　　　　　　　　　　　　　　　　　　　　　　　10µM ICG-001

Differentiation Medium　　　　　Growth Medium +
　　　　　　　　　　　　　　　　　10µM ICG-001

A.

FC-A (FC)

C36H56O12
Exact Mass: 680.3772
Mol. Wt.: 680.8226

B.

FC-J

C32H52O9
Exact Mass: 580.3611
Mol. Wt.: 580.7499

C.

CN-A (CN)

C33H50O11
Exact Mass: 622.3353
Mol. Wt.: 622.7435

MODULATION OF BETA-CATENIN COACTIVATOR INTERACTIONS TO EFFECT STEM CELL GROWTH OR DIFFERENTIATION

RELATED APPLICATIONS

The present invention claims benefit of priority from U.S. Provisional Patent Application Ser. No. 60/663,363 filed Mar. 18, 2005, under 35 U.S.C. § 119. The foregoing provisional patent application is incorporated herein by reference in its entirety.

BACKGROUND OF THE INVENTION

1. Field of the Invention

The present invention relates to compounds and methods for modulating the interaction between β-catenin or γ-catenin and the coactivator protein CBP, or β-catenin or γ-catenin and the coactivator protein p300, to promote proliferation/dedifferentiation or differentiation of stem/progenitor cells.

2. Description of the Related Art

Stem cells have received significant interest over the last few years due to their potential, under suitable cellular microenvironments, to differentiate and develop into a wide array of cell and tissue types. Several important biomedical applications would be enabled by the ability to generate sufficient pools of adult stem cells, including cell replacement therapy, gene therapy, and tissue engineering. According to the National Institutes of Health, the therapeutic use of stem cells will become a cornerstone of medicine within the next two decades:

> Given the enormous potential of stem cells to the development of new therapies for the most devastating diseases, when a readily available source of stem cells is identified, it is not too unrealistic to say that this research will revolutionize the practice of medicine and improve the quality and length of life (National Institutes of Health. Stem Cells: Scientific Progress and Future Research Directions. Jun. 17, 2001.). However, the development of such applications for adult stem cells has been severely impaired due to the inability to propagate and expand functional adult stem cells in culture. To date, this has proven to be a singular challenge in stem cell research (Sherley, J. (2002) *Stem Cells,* 20:561-572). For decades, scientists have attempted to grow stem cells in culture to increase the number of cells for transplantation. The challenge of this undertaking lies in the stem cell's predisposition to differentiate. This problem may be associated with the inherent asymmetric cell kinetics of stem cells in postnatal somatic tissues (Sherley, J. (2002) *Stem Cells,* 20:561-572). Existing scientific methods used for increasing the number of stem cells include culturing cells on 2-D stromal layers and growing them in the presence of various cytokine cocktails (Rebel, V I., et al. (1994) *Blood,* 83(1):128-136). However, none of the existing ex vivo methods can prevent differentiation of stem cells while promoting proliferation (Rebel, V I. et al. (1996) *J Hematother.* 5(1):25-37). There is therefore a need in the art for compounds and methods for use in propagating and expanding adult stem cells in culture.

BRIEF SUMMARY OF THE INVENTION

The invention relates to compounds and methods for modulating the interaction between β-catenin (or γ-catenin) and the coactivator proteins CBP and p300 to either promote proliferation/or differentiation of stem/progenitor cells.

The compounds of the present invention either increase or decrease post-translational modifications (i.e. phosphorylation, acetylation, sulfonylation, glycosylation) of CBP, p300, or β- or γ-catenin thereby modulating the selection of coactivator usage by catenin.

The invention also relates to methods for enhancing the proliferation of mammalian stem cells, by administering to the stem cells an agent that selectively modulates the interaction of β-catenin with CBP or p300.

The invention further relates to a method for modulating the interaction of β-catenin with CBP or p300 in a cell, comprising treating the cell with an agent that affects the post-translational modifications of at least one of CBP or p300 or β-catenin, thereby selectively modulating the interaction of β-catenin with CBP or p300, wherein said agent does not directly bind to CBP or p300.

In an embodiment of this method, the agent increases the binding of β-catenin to CBP.

In a further embodiment of the method, the agent decreases the binding of p300 to β-catenin.

In yet further embodiments of the method, the agent increases the binding of p300 to β-catenin, or the agent decreases the binding of CBP to β-catenin.

The cell may be treated with the agent of the invention ex vivo and the cell may be a stem cell/progenitor cell.

In certain embodiments, the agent is applied topically to a mammal comprising said cell.

In further embodiments the agent increases the binding of β-catenin to the amino-terminal 110 amino acids of CBP or decreases the binding of β-catenin to the amino-terminal 110 amino acids of p300.

In specific embodiments, the agent decreases the binding of β-catenin to the amino-terminal 110 amino acids of p300 by inhibiting the phosphorylation of Ser 89 of p300, such as by a serine protein kinase; the serine protein kinase may be PKC or CaMK. CaMK kinases may phosphorylate different residues in this N-terminal region, for example Ser 89, Ser 24. The protein kinase may also be PAR-1 or PAR-4, acting either directly or via a kinase cascade.

In further specific embodiments, the agent decreases the binding of β-catenin to the amino-terminal 110 amino acids of p300 by inhibiting the phosphorylation of Ser 89 of p300 by increasing the phosphorylation of Ser 90 of p300, such as by a serine protein kinase; the serine protein kinase may be MAPK or CDK.

In other specific embodiments, the agent modulates the interaction of Ser 89 phosphorylated p300 with a 14-3-3 protein, and the agent may be an analog of Fusicoccin, wherein the analog of Fusicoccin has the following general formula:

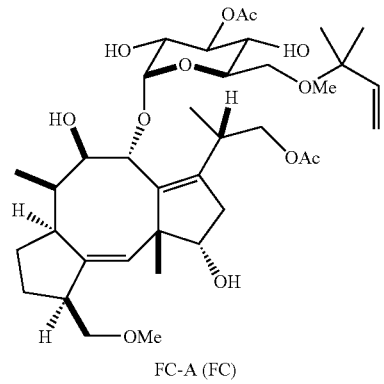

FC-A (FC)

The invention also relates to a method of modulating the interaction of β-catenin with CBP or p300 in a cell, wherein the agent modulates the interaction of prolyl isomerase (Pin1) with β-catenin, CBP or p300; in certain embodiments, the agent increases the association of Pin1 with CBP.

In all these embodiments, the agent may be incorporated into a biomaterial capable of supporting the growth of a stem cell; the stem cell may be a hematopioetic stem cell.

The invention also relates to a compound having the following general formula (I) and uses thereof to modulate stem cell proliferation, in particular to enhance proliferation:

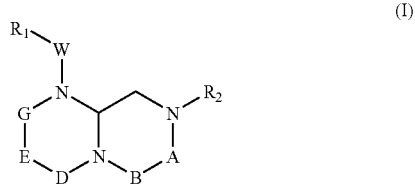

(I)

wherein A is —(CHR$_3$)—(C═O)—. B is —(NR$_4$)—, D is —(CHR$_5$)— or —(C═O)—, E is —(ZR$_6$)—, —(C═O)—, G is —(XR$_7$)$_n$—, —(CHR$_7$)—(NR$_8$)—, —(C═O)—(XR$_9$)—, or —(C═O)—, W is —Y(C═O)—, —(C═O)NH—, —(SO$_2$)— or nothing, Y is oxygen or sulfur, X and Z is independently nitrogen or CH, n=o or 1; and R$_1$, R$_3$, R$_4$, R$_5$, R$_6$, R$_7$, R$_8$, R$_9$, R$_{10}$, and R$_{11}$ are the same or different and independently selected from an amino acid side chain moiety or derivative thereof, the remainder of the molecule, a linker and a solid support, and stereoisomers thereof. R2 is selected from a monocyclic aryl or heteroaryl moiety bearing the substituent NR$_{10}$R$_{11}$, wherein the compound binds preferentially to p300 phosphorylated at Ser89.

The invention further relates to a method of enhancing the proliferation of a mammalian stem cell, comprising administering to the stem cell an agent that selectively modulates the interaction of β-catenin with CBP or p300; the agent may increase the binding of β-catenin to CBP; and the agent may decrease the binding of β-catenin to p300.

The administration to the stem cell may be ex vivo, and the stem cells may be hematopoietic stem cells, hair cells, neural stem cells, or pancreatic islet cells.

DETAILED DESCRIPTION OF THE INVENTION

Figure 1:
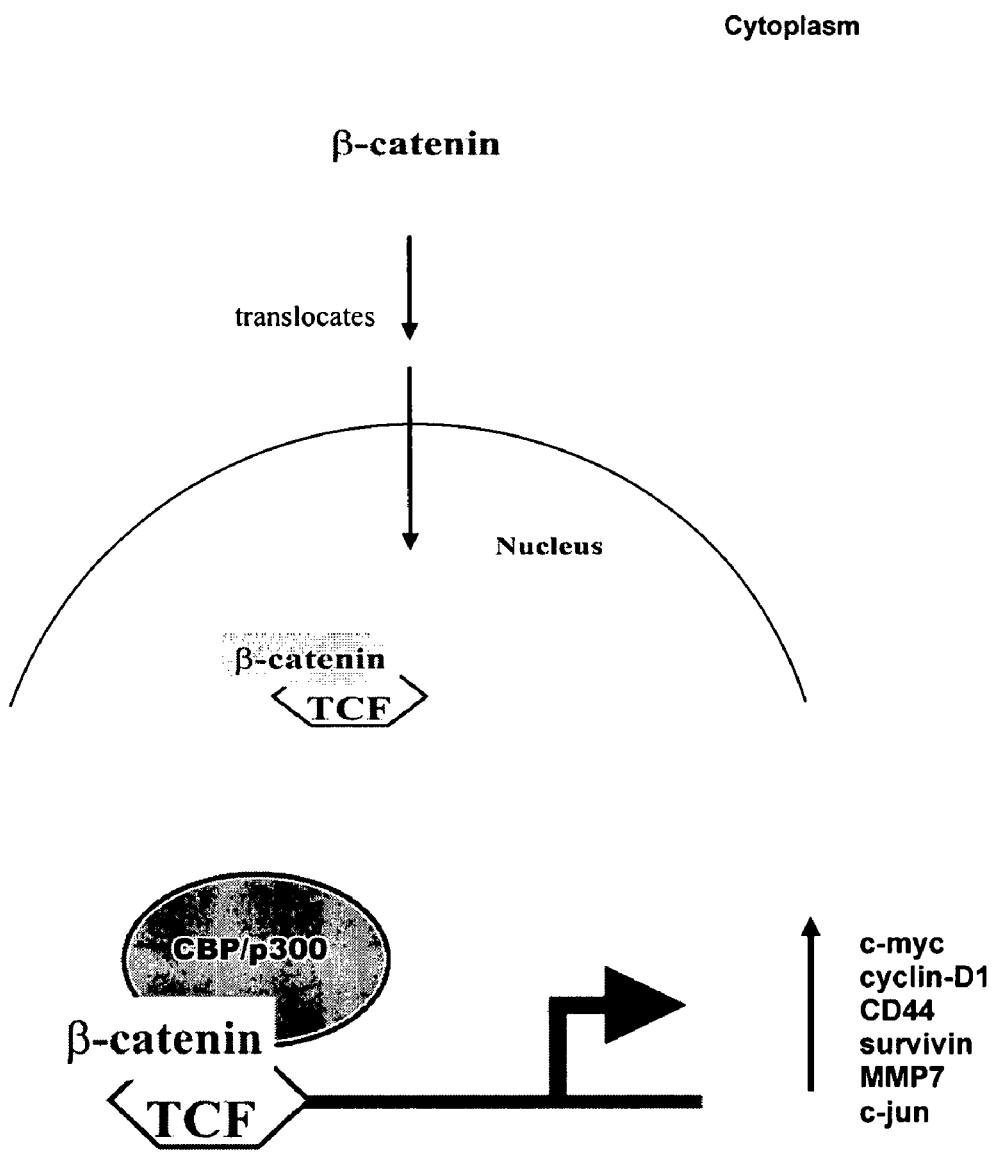
FIG. 1 is a schematic representation of TGF/β-catenin transcription.

Stem cells are responsible for the regeneration and maintenance of tissues by balancing the processes of self-renewal (i.e., making new stem cells) and differentiation (i.e., generating cells committed to terminal differentiation). This balance results from integration of regulatory signals intrinsic to the stem cell, as well as extrinsic signals from the microenvironment. Perturbations in the balance between self-renewal and differentiation may result in disease, either as a result of stem cell depletion (e.g., aplastic anemia) or increased self-renewal (e.g., cancer).

Most knowledge about the molecular mechanisms of stem cell regulation in mammals has been derived from studies of the hematopoietic system. There is an extensive and expanding understanding of the molecular mechanisms that regulate differentiation along the terminal lineages. However, a mechanistic understanding of the mechanisms that regulate hematopoietic stem cell (HSC) fate decisions is less well understood. A few genes have been identified that, when deleted, result in perturbation of HSC self-renewal (e.g. TNFα-p55-Receptor, p21, Rae28, and Bmi-1) or altered differentiation (e.g., TEL, PU.1, Flt-3, and p27). HoxB4, β-catenin, and Notch signaling, on the other hand, stimulate HSC self-renewal when over-expressed in HSCs.

Recent work has demonstrated that CBP and p300 play important roles in HSC self-renewal and differentiation. CBP and p300 function as molecular integrators of various transcriptional signals. When recruited to promoters by transcription factors, they function as co-activators of transcription through multiple mechanisms, including chromatin remodeling, acetylation of associated proteins, and recruitment of the basal transcription machinery. CBP and p300 are highly homologous on a structural level, with up to 93% identity within certain protein-binding domains (SEQ ID NO:1 and 2). For most functions, the two proteins appear to be functionally redundant. However, mouse genetic loss-of-function studies demonstrated a difference between p300 and CBP function in HSCs: loss of CBP results in defective HSC self-renewal, whereas loss of p300 results in defective hematopoietic differentiation.

CBP and p300 have been previously shown to interact with many of the known transcription factors shown to be important in HSC regulation (e.g., HoxB4, β-catenin, Notch, AML-1, MLL). Earlier results suggest that within HSCs there may be transcription factors that are specifically co-activated by CBP that are critical for self-renewal, and others that are preferentially co-activated by p300 that are critically required for differentiation. One example of a signaling pathway that seems to utilize CBP and p300 differentially is the Wnt signaling pathway. The Wnt signaling pathway has been shown to play a pertinent role in the development and maintenance of various tissues, including blood, intestines, and skin. Its effects are executed at the level of stem and progenitor cells, affecting both self-renewal and differentiation. Moreover, the importance of Wnt signaling in maintaining the undifferentiated features of embryonic stem (ES) cells has been well established. Importantly, when Wnt signaling is perturbed it can lead to the development of cancer in these same tissues.

β-catenin (SEQ ID NO:3) is a vertebrate homolog of Drosophila gene armadillo, which functions in both cell adhesion and, as discussed herein, the Wnt signaling pathway. γ-catenin (SEQ ID NO:4) is also a vertebrate homolog of armadillo. β-catenin and γ-catenin have analogous structures and functions, and they have the ability to be regulated by the APC tumor suppressor.

Activation of the Wnt signaling pathway requires the nuclear stabilization of TCF (T cell actor)/β-catenin complexes and recruitment of transcriptional co-activators, such as CBP and p300. β-catenin is constitutively produced in the cell, and inhibitory mechanisms exist to maintain β-catenin levels at below those that would lead to aberrant transcriptional activity in vivo, leading to pathological conditions such as cancer. In one example of aberrant regulation, Emami and colleagues (PNAS101: 12682-7, 2004) recently demonstrated that β-catenin preferentially associates with CBP in cancer cells. However, when β-catenin was prevented from associating with CBP, by utilizing a β-catenin/CBP-specific inhibitor, β-catenin could bind to p300. The "alternative" binding of β-catenin to p300 was accompanied by the execution of a differentiative genetic program (Teo J et al. PNAS, 102, 2005). Thus, β-catenin is thought to promote proliferation without differentiation by binding to and activating CBP, and to initiate differentiation with limited proliferation by binding to and activating p300. Perturbation of β-catenin interaction with CBP and/or p300 is expected therefore to influence differentiation or proliferation.

Stem cell therapy is based on the ability of human fetal or adult pluripotent stem cells to differentiate into a variety of cell types. Stem cells may be used to replace damaged cells as a treatment for many different diseases including cancer, Parkinson's disease, spinal cord injury, burns, diabetes, heart disease, rheumatoid arthritis, and osteoarthritis and for gene therapy (Lazic, S E. et al. *J Hematother Stem Cell Res*, 12(6): 635-642, Gafni, Y. et al. *Gene Ther.* 11(4):417-426). Stem cell therapy has long been an exciting potential medical breakthrough. The ability to inject normal stem cells into a patient, where they could generate organ-specific cells to potentially replace defective patient tissues, offers enormous potential.

The ability to maintain adult skin stem cells in vitro has allowed engraftment of cultured skin onto burn victims (Green, H. (1991) *Sci. Am.* 265:96-102). Additionally, at present, there are three adult stem cell related transplantation procedures used for hematopoietic reconstitutution: bone marrow transplantation (BMT), peripheral blood stem cell transplantation (PBSCT) and umbilical cord blood stem cell transplantation (UCBSCT). The first two hematopoietic reconstitution techniques, BMT and PBSCT, suffer from a significant matching problem with allogeneic donors. The degree of match required for a successful transplant appears to be less stringent for UCBSCT than BMT or PBSCT. However, the relatively lower volume of harvested stem cells and the availability of only one collected cord blood unit per transplant procedure limit the wide applicability of UCBSCT (McCaffrey, P. *Lancet Oncol.*, 6(1): 5, 2005). One solution to this problem is ex vivo expansion of the cord blood stem cells. However, there is a significant hurdle to overcome in order to provide this straightforward solution.

Stem Cells and Cancer "Stem Cells"

A unifying feature of all cancers is their capacity for unlimited self-renewal, which is also a defining characteristic of normal stem cells. Decades ago, it was discovered that the proliferative capacity of all cancer cells was not equivalent, and only a small minority of tumor cells were able to proliferate extensively (Hamburger, A. W. et al. (1977) *Science*, 197(4302):461-463). This gave rise to the concept that malignant tumors are comprised of *Cancer Stem Cells*, which have great proliferative potential, as well as another pool of more differentiated cancer cells, with limited proliferative capacity. An important implication of the *Cancer Stem Cell* hypothesis is that there are mechanistic similarities between the self-renewal of normal stem cells and the proliferation of cancer stem cells (Pardal, R. et al. (2003) *Nat. Rev. Cancer* 3(12): 895-902). Recent studies have demonstrated that specific gene products regulate both the self-renewal of normal somatic stem cells, as well as the proliferation of cancer cells (Park, I. K. et al. (2003) Nature 423:302-305; Lessard, J. et al. (2003) *Nature*, 423(6937):255-260). This implies that similar mechanisms are utilized in both stem cells and cancer cells to maintain a proliferative, non-differentiated state.

Wnt Signaling in Stem Cells and Cancer

The Wnt/β-catenin pathway initiates a signaling cascade critical in both normal development and the initiation and progression of cancer (Giles, R H et al. (2003) *Biochim Biophys Acta*, 1653(1):1-24; Wodarz, A. et al. (1998) *Annu Rev Cell Dev Biol*, 14:59-88). Wnt signaling and in particular the nuclear functions of β-catenin have been shown to be important in the maintenance, proliferation as well as the differentiation of stem cells (Song, X. et al. (2003) *Development*, 130(14):3259-3268). Some of the salient features of this signaling pathway, relevant to this invention, are summarized in FIG. 1. The Wnt/β-catenin pathway normally regulates expression of a range of genes involved in promoting both proliferation and differentiation. Activation of the Wnt pathway allows β-catenin to accumulate in the nucleus, bind to members of the TCF family of transcription factors, and form a transcriptionally active complex, by recruiting either the transcriptional coactivator CBP or its closely related homolog, p300. However, in greater than 85% of colon cancers, mutations in this pathway lead to constitutive activation and expression of target genes, e.g. c-myc, cyclin D1 and survivin, all of which are critical for rapid cell proliferation (Kolligs, F T. et al. (1999) *Mol Cell Biol*, 19(8):5696-5706; Tetsu, O. et al. (1999) *Nature*, 398(6726):422-426; Kim, P J. et al. (2003) *Lancet*, 362:205-209). Thus, tumorigenesis in the intestinal epithelium appears to be caused by Wnt/β-catenin induced hyper-proliferation of intestinal crypt stem cells, followed by accumulation of additional mutations that confer malignancy and cancer progression. Wnt signaling has also been demonstrated to be important for the maintenance of pluripotency in both mouse and human embryonic stem cells in culture (Sato, N. et al. (2004) *Nat Med*, 10(1):55-63). Expression of multiple components of the Wnt pathway is evident in the P19 human embryonal carcinoma cell lines, as well as in embryonic stem cells (Walsh, J. et al. (2003) *APMIS*, 111(1):197-211).

Wnt and Hematopoietic Stem Cells (HSC)

The self-renewal of hematopoietic stem cells (HSC) is also promoted by Wnt signaling. Overexpression of stabilized β-catenin in cultured bone marrow HSC from mice increased the number of these cells in long-term culture as measured by their ability to reconstitute the hematopoietic systems of mice following irradiation. Additionally, purified Wnt3a promoted self-renewal but only partially inhibited the differentiation of HSC in culture (Reya, T. et al. (2003) *Nature*, 423(6938):409-414).

Differential Coactivator Usage in Wnt/β-catenin Signaling

As discussed above, the functions of CBP and p300 have been described as redundant in several studies (reviewed in Goodman, R H. et al. (2000) *Genes Dev*, 14(13):1553-1577) and their expression pattern during mouse development is almost identical (Partanen, A. et al. (1999) *Int JDev Biol*, 43(6):487-494). However, it is becoming increasingly clear that these highly homologous coactivators are not redundant under physiological conditions, and are responsible for distinct transcriptional programs. Rebel et al. (Rebel, V I. et al. (2003) *Proc Natl Acad Sci USA*, 99(23):14789-14794), using cells from knockout mice, demonstrated that a full dose of CBP, but not p300, is crucial for HSC self-renewal. Conversely, p300 but not CBP, is essential for proper hematopoietic differentiation. Similarly, Eckner and colleagues (Roth, J F. et al. (2003) *Embo J*, 22(19):5186-5196) demonstrated a critical role for p300's histone acetyltransferase activity (HAT) but not CBP's HAT activities. These studies and others clearly demonstrate that CBP and p300 play non-redundant and distinct roles during development.

Figure 2:
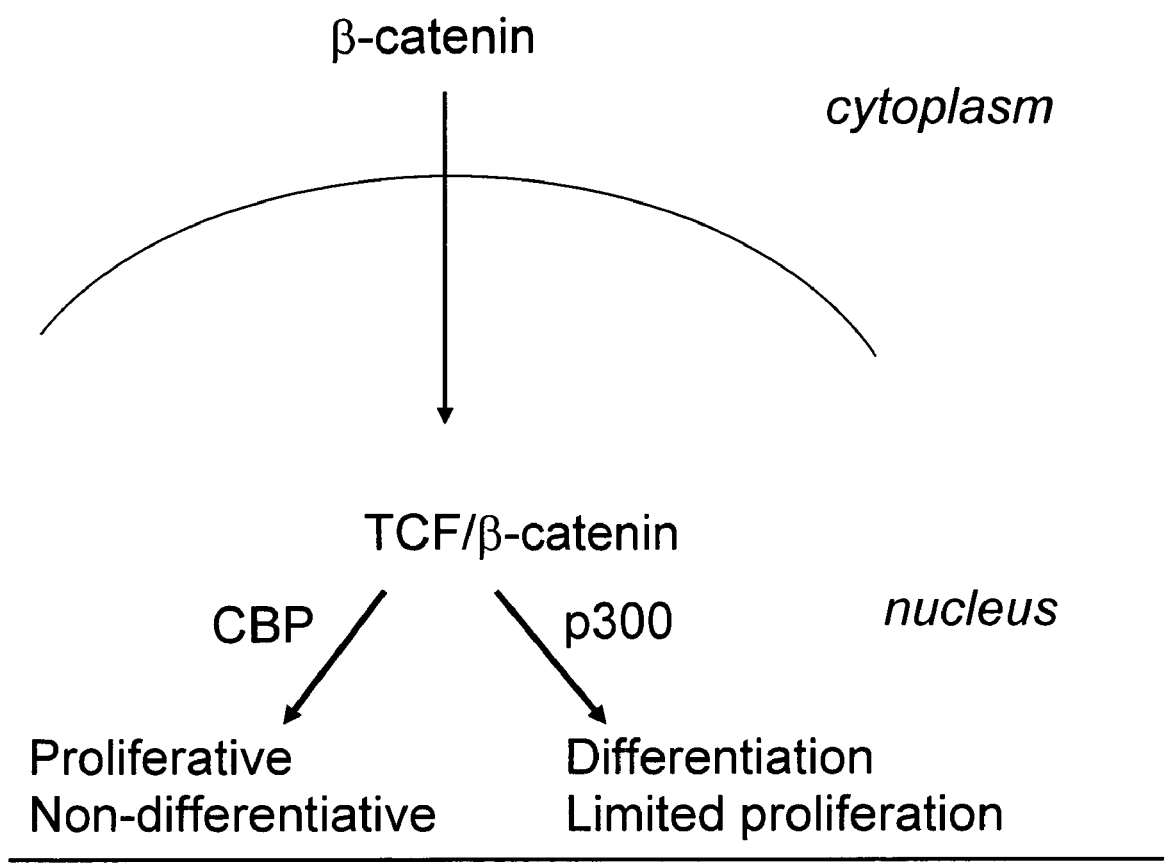
FIG. 2 is a schematic representation of two possible mechanisms of action of β-catenin, resulting from alternative interaction with CBP or p300 in the nucleus.
Figure 3:
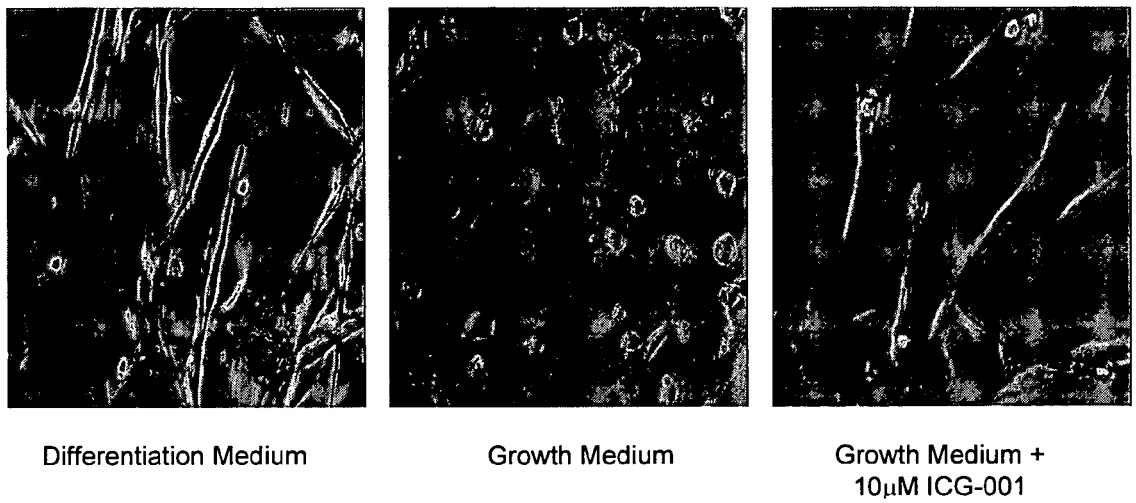
FIG. 3 illustrates that ICG-001 at 10 μM concentration induces the differentiation of C2C12 myeloblasts, as compared to differentiation medium or growth medium.
Figure 4:
FIG. 4 illustrates that differentiation of C2C12 myeloblasts is induced by 10 μM ICG-001 as compared to differentiation medium.

From our chemogenomic studies with the small molecule inhibitor of the β-catenin/CBP interaction and additional gene expression profiling, we have developed a model that describes how differential coactivator usage in Wnt signaling controls proliferation vs. differentiation. The critical feature of this model is that the CBP arm (FIG. 2, left side) of the pathway is essential for proliferation without differentiation, for example in cancer or stem cells, whereas the p300 arm (FIG. 2, right side) is critical for differentiation, with limited proliferation. ICG-001 specifically inhibits β-catenin/CBP dependent transcription (i.e. the left arm of the pathway), thus selectively inducing programmed cell death in cancer cells (Emami, K H. et al. (2004) *Proc Natl Acad Sci USA,* 101, 12682-7, 2004), and inducing the differentiation of non-tumorigenic precursor cells, e.g. C2C12 myoblasts (FIGS. 3, 4) and 3T3-L1 preadipocytes.

Without being bound by a specific mechanism, the invention is based on the premise that selectively inhibiting or down-modulating the β-catenin/p300 interaction (i.e. the right side of the pathway, FIG. 2) allows for proliferation without differentiation of pluripotent stem cells.

For maintenance of hematopoietic stem cell proliferation, a preferable agent of the invention is capable of affecting the post-translational modifications of any one of CBP, p300, or β-catenin, leading to a selective increase of β-catenin interaction with CBP or a selective decrease of β-catenin interaction with p300, wherein the agent does not directly bind to CBP or p300. In one embodiment, the agent increases the binding of β-catenin to CBP. In another embodiment, the agent decreases the binding of β-catenin to p300. With either of these embodiments, the overall result biases the B-catenin pathway towards "proliferative/non-differentitive program" of the target cells, which according to the invention are adult stem cells, such as hematopoietic stem cells, neural stem cells, or skin stem cells. For example, with reference to FIG. 2, preferential binding of β-catenin to CBP, with less binding to p300, is associated with maintaining hematopoietic stem cells in an undifferentiated state wherein they undergo continuous proliferation, resulting in enhanced numbers of undifferentiated cells useful for repopulating the hematopoietic system of a mammal, such as a human, in need of such treatment.

Agents suitable for use according to the invention can be screened using co-immunoprecipitation methods as described in Emami et al. PNAS101:12682-7, 2004. Briefly, target cells, in this case HSC, are transfected with full-length β-catenin or with full-length p300. Nuclear lysates are treated with a radiolabeled test agent alone, or with cold test agent. Unbound radiolabeled test agent is removed, and incorporation of the radiolabeled test agent is measured. The results indicate whether the test agent specifically interacts with p300.

A separate series of experiments can demonstrate inhibition of the interaction of β-catenin with p300. The minimal binding domain of CBP (amino acids 1-111), p300 (amino acids 1-111) and the C-terminal region of β-catenin (SEQ ID NO:3) (amino acids 647-781) are expressed in mammalian cells treated with the appropriate agents to modify the interaction and purified. β-catenin is bound to protein A-agarose beads coated with β-catenin-specific antibody and incubated with either CBP or p300. Unbound proteins are removed by washing, then the specific interactions between β-catenin and p300, and β-cateninand CBP, are challenged using the test agent, for testing the compounds which directly bind to CBP or phosphor Ser89 p300. Agents that either increase the binding of β-catenin to CBP or decrease the binding of β-catenin to p300 are further tested in vitro using a suitable model of hematopoietic stem cell proliferation/differentiation. One such model is described in Rebel, V. I. et al., PNAS 99:14789-14794, 2002.

Agents according to the invention may achieve the desired biological effects through one of several mechanisms. For example, the agent may increase the binding of β-catenin to the amino-terminal 110 amino acids of CBP, or it may decrease the binding of β-catenin to the amino-terminal 110 amino acids of p300. The decrease in binding of β-catenin to p300 may be achieved by inhibiting the phosphorylation of Ser 89 of p300, wherein the phosphorylation is catalyzed by protein kinase C-epsilon (PKC), calcium/calmodulin-dependent protein kinase (CaMK), LKB (PAR-4), AMP activated kinase (PAR-1), or other serine/threonine protein kinase either directly or indirectly via a kinase cascade.

The decreased phosphorylation of Ser 89 of p300 may be achieved by increasing the phosphorylation of Ser 90, for example by mitogen-activated protein kinase 4 (MAPK), cyclin-dependent kinase (CDK), or other serine/threonine protein kinase (eg. PI3K).

Figure 5:
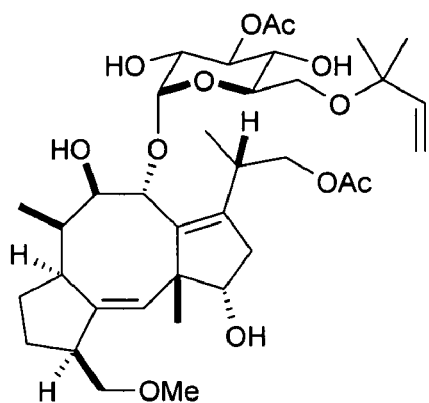
FIG. 5A illustrates the structure of Fusicoccin A (FC-A).
FIG. 5B illustrates the structure of Fusicoccin J (FC-J).
FIG. 5C illustrates the structure of cotylenin A (CN-A).
Figure 5:
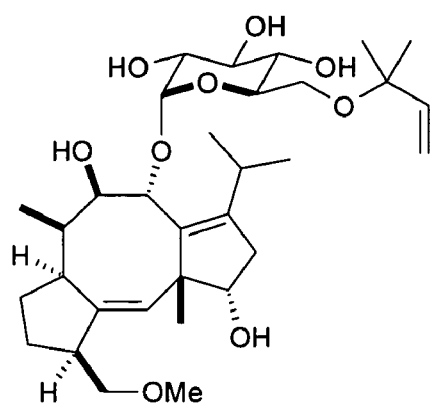
Figure 5:
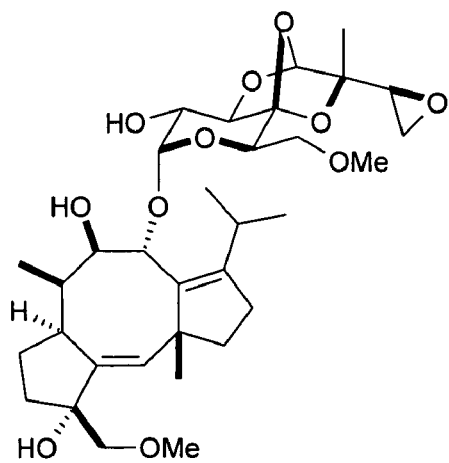

A preferable agent of the invention may modulate the interaction of Ser 89-phosphorylated p300 with 14-3-3 proteins. Such agents may be analogs of Fusicoccin, such as Fusicoccin A, Fusicoccin J, and cotylenin A. The structures of Fusicoccin A, Fusicoccin J, and cotylenin A are shown in FIG. 5. Fusicoccin is a fungal toxin that is used to study H+-ATPase activation. The mechanism involves inducing an irreversible bond between the C-terminal portion of H+-ATPase, and 14-3-3 protein. (Svennilid, F. et al., Plant Cell 11:2379-2392, 1999.) As a result, the C-terminal auto-inhibiting domain is displaced. Similarly, analogs of Fusicoccin may modulate the interaction of Ser-89 phosphorylated p300 with 14-3-3 proteins, resulting in the decreased interaction of p300 with β-catenin.

In other embodiments, the agent modulates the interaction of Pin1 with β-catenin or with CBP or p300. In one embodiment of the invention, the agent increases the association of Pin1 with β-Catenin/CBP. Pin1 (prolyl isomerase) has been implicated in cancer mechanisms by inhibiting the interaction of β-catenin with the tumor suppressor APC. Pin1 overexpression has been reported to occur in human breast cancer. (Ryo, A. et al., Nat. Cell Biol. 3:793-801 (2001)). Pin1 has also been implicated in normal spermatogenesis. Atchison, F. W. et al. (Biol. Reprod. 69:1989-1997, 2003) reported that adult Pin1-deficient mice exhibited evidence of accelerated exhaustion of stem cell potential, and possible bias towards the differentiation pathway in the absence of Pin1.

Phosphorylation affects the conformation of proteins and creates conditions for binding of signal transducers to certain suitable domains capable of recognizing the phosphorylated residue or residues. Pin1 specifically recognizes phosphorylated S/T—P bonds (Ser/Thr-Pro motifs). For example, Pin1 directly binds a phosphorylated Ser-Pro motif (Ser 246-Pro) next to the APC-binding site in β-catenin, inhibits β-catenin interaction with adenomatous polyposis coli protein (APC), and thereby increases its translocation into the nucleus. (Ryo, A. et al., Nature Cell Biol. 3:793-801, 2001.)

Pin1 can also affect coactivator interactions with transcription factors. P73 is a transcription factor related to the tumor suppressor p53. Pin1-modified p73 displayed a higher affinity for p300 than unmodified p73. (Montovani, F. et al., Mol. Cell. 14:625-636, 2004.) Similarly, Pin1 binding to phosphorylated β-catenin can increase the β-catenin/CBP interaction and thereby β-catenin/CBP dependent gene transcription promoting proliferation at the expense of differentiation.

The agents of the invention can be incorporated into biomaterials on which hematopoietic stem cells are grown. Examples are disclosed in Horak et al. Biomaterials 25, 5249-60, 2004 and Harrison et al. Biomaterials 25, 4977-86, 2004.

Although hematopietic stem cells are disclosed herein as an embodiment of a target for the methods of the invention, the methods are applicable to any adult mammalian stem cells (or ES cells) that can be used for tissue regeneration. Adult stem cells constitute an undifferentiated population of cells that retain the ability to proliferate throughout postnatal life and to differentiate into specialized cells to replace cells that become diseased, die or are lost. (Agrawal, S. et al; Trends in Biotechnology 23:78-83, 2005.) In addition to HSC, stem cells suitable for use according to the invention include neural stem cells, skin stem cells, muscle stem cells, and pancreatic islet cells.

The goal of diabetes treatment is to restore normal numbers and function of insulin-producing β cells. Trucco, M. (J. Clin. Invest. 115:5-12, 2005) discusses the existence of adult pancreatic precursor cells that can generate β cells, and are referred to as pancreas-derived multipotent precursors. Other stem cells may be induced to direct their differentiation toward the β cell. For either of these sources of β cells, the methods and agents of the invention are suitable for inducing proliferation and limiting differentiation, in order to achieve a suitable number of cells for therapeutic use.

Adult neural stem cells can differentiate into neurons, astrocytes, and oligodendrocytes, which are the three major lineages of the adult nervous system. For such applications of the invention, it may be appropriate to manipulate adult neural stem cells in situ in order to achieve neurogeneration in vivo. Active stem cells exist in adult brain in the dentate gyrus region of the hippocampus and the subventricular zone of the forebrain, and these stem cells can differentiate into neurons, astrocytes and oligodendrocytes. In addition, quiescent stem cell pools exist in the spinal cord, substantia nigra, optic nerve, and hypothalmus. (Agrawal, S. et al., 2005). Thus, defined pools of neural stem cells are available for modulation according to the invention.

Skin stem cells may be induced to proliferate in vivo in order to enhance or restore hair growth. Recent evidence suggests that the Wnt pathway is involved in the ability of skin epithelial cells to acquire and/or maintain characteristics of multipotent stem cells. (Alonso, L. et al.; PNAS 100:11830-11835, 2003). Multipotent stem cells in skin receive Wnt signals before they commit to form hair follicles. In transgenic mouse skin in which β-catenin is constitutively stabilized, adult interfollicular epidermis takes on characteristics of embryonic skin, and may have the capacity to develop into hair follicles. (Gat, V., Cell 95:605-614, 1998). Thus, agents and methods of the invention are suitable for enhancing the proliferation of multipotent stem cells in the skin, to provide a reservoir of cells capable of forming hair follicles in order to increase or replace lost hair growth, including in vivo applications, for example by topical use. U.S. Pat. No. 6,419,913 discloses compositions suitable for topical delivery of therapeutic agents including agents for treatment of hair loss. U.S. Pat. No. 6,680,344 also discloses topical delivery of agents for treating hair loss.

In addition to using stem cells following proliferation induced by the agents and methods of the invention, it is also feasible to alter the stem cells prior to use, by gene therapy. The invention therefore provides methods to enhance the proliferation of mammalian stem cells expressing an exogenous gene, prior to administration of the cells for therapeutic use. The gene therapy may also be conducted in vivo, for example, to alter the differentiation potential of neural stem cells. (Gomes, W. A. et al., Dev. Biol. 255:164-177, 2003; Pardridge, W. M., Curr. Opin. Drug Discov. Devel. 6:683-691, 2003.)

An assay suitable for determining whether mammalian stem cells are maintained in a non-differentiated state involves the use of a reporter gene under the control of the OCT4 promoter. OCT4 is a known marker of the undifferentiated stem/progenitor cell state, and the promoter region can be functionally linked to a reporter gene such as EGFP (enhanced green fluorescent protein) as described in Gerrard, L. et al., Stem Cells 23:124-133 (2005), or luciferase. Using either reporter gene, cells are transfected with an OCT4-reporter gene construct using methods described in Gerrard et al. (2005) and the effect of agents according to the invention on the undifferentiated versus differentiation state of the cells is tested.

Methods for testing the effect of small molecules on stem cells in vitro include those described by Chen, J. K. et al., P.N.A.S. 99:14701-14076 (2002) and Frank-Kamenetsky, M. et al., J. Biol 1:10 (2002).

Agents for use in the invention include a α-helix mimetic structure having the following formula (I):

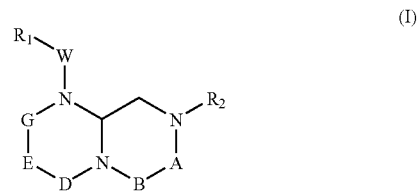

(I)

wherein A is —(C=O)—(CHR$_3$)—, B is —N—R$_4$—, D is —(CHR$_5$)— or —(C=O)—, E is —(ZR$_6$)— or —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or nothing, Y is oxygen or sulfur, X and Z is independently nitrogen or CH, n=0 or 1; and R$_1$, R$_2$, R$_3$, R$_4$, R$_5$, R$_6$, R$_7$, R$_8$ and R$_9$, are the same or different and independently selected from an amino acid side chain moiety or derivative thereof, the remainder of the molecule, a linker and a solid support, and stereoisomers thereof.

More specifically, R$_1$, R$_2$, R$_3$, R$_4$, R$_5$, R$_6$, R$_7$, R$_8$ and R$_9$, are independently selected from the group consisting of aminoC$_{2-5}$alkyl, guanidineC$_{2-5}$alkyl, C$_{1-4}$alkylguanidinoC$_{2-5}$alkyl, diC$_{1-4}$alkylguanidino-C$_{2-5}$alkyl, amidinoC$_{2-5}$alkyl, C$_{1-4}$alkylamidino C$_{2-5}$alkyl, diC$_{1-4}$alkylamidinoC$_{2-5}$alkyl, C$_{1-3}$alkoxy, Phenyl, substituted phenyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-3}$alkyl, nitro, carboxy, cyano, sulfuryl or hydroxyl), naphthyl, substituted naphthyl (where the substituents are independently selected from one or more of amino, amidino, guanidino, hydrazino, amidrazonyl, C$_{1-4}$alkylamino, C$_{1-4}$dialkylamino, halogen, perfluoro C$_{1-4}$alkyl, C$_{1-4}$alkyl, C$_{1-3}$alkoxy, nitro, carboxy, cyano, sulfuryl or hydroxyl), bisphenyl methyl, substituted bis-phenyl methyl (where the subsitituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl, sustituted pyridyl, (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl$C_{1-4}$alkyl, substituted pyridyl$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyrimidyl$C_{1-4}$alkyl, substituted pyrimidyl$C_{1-4}$alkyl (where the pyrimidine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), triazin-2-yl-$C_{1-4}$alkyl, substituted triazin-2-yl-$C_{1-4}$alkyl (where the triazine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazo$C_{1-4}$alkyl, substituted imidazol $C_{1-4}$alkyl (where the imidazole substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazolinylCalkyl, N-amidinopiperazinyl-N—$C_{0-4}$alkyl, hydroxy$C_{2-5}$alkyl, $C_{1-5}$alkylamino$C_{2-5}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl.

In one embodiment, $R_1$, $R_2$, $R_6$ of E, and $R_7$, $R_8$ and $R_9$ of G are the same or different and represent the remainder of the compound, and $R_3$ or A, $R_4$ of B or $R_5$ of D is selected from an amino acid side chain moiety or derivative thereof. As used herein, the term "remainder of the compound" means any moiety, agent, compound, support, molecule, linker, amino acid, peptide or protein covalently attached to the α-helix mimetic structure at $R_1$, $R_2$, $R_5$, $R_6$, $R_7$, $R_8$ and/or $R_9$ positions. This term also includes amino acid side chain moieties and derivatives thereof.

As used herein, the term "amino acid side chain moiety" represents any amino acid side chain moiety present in naturally occurring proteins including (but not limited to) the naturally occurring amino acid side chain moieties identified in Table 1. Other naturally occurring amino acid side chain moieties for use in this invention include (but are not limited to) the side chain moieties of 3,5-dibromotyrosine, 3,5-diiodotyrosine, hydroxylysine, γ-carboxyglutamate, phosphotyrosine and phosphoserine. In addition, glycosylated amino acid side chains may also be used in the practice of this invention, including (but not limited to) glycosylated threonine, serine and asparagine.

TABLE 1

Amino Acid Side Chain Moieties

| Amino Acid Side Chain Moiety | Amino Acid |
| --- | --- |
| —H | Glycine |
| —$CH_3$ | Alanine |
| —$CH(CH_3)_2$ | Valine |

TABLE 1-continued

Amino Acid Side Chain Moieties

| Amino Acid Side Chain Moiety | Amino Acid |
| --- | --- |
| —$CH_2CH(CH_3)_2$ | Leucine |
| —$CH(CH_3)CH_2CH_3$ | Isoleucine |
| —$(CH_2)_4NH_3^+$ | Lysine |
| —$(CH_2)_3NHC(NH_2)NH_2^+$ | Arginine |
|  | Histidine |
| —$CH_2COO^-$ | Aspartic acid |
| —$CH_2CH_2COO^-$ | Glutamic acid |
| —$CH_2CONH_2$ | Asparagine |
| —$CH_2CH_2CONH_2$ | Glutamine |
|  | Phenylalanine |
|  | Tyrosine |
|  | Tryptophan |
| —$CH_2SH$ | Cysteine |
| —$CH_2CH_2SCH_3$ | Methionine |
| —$CH_2OH$ | Serine |
| —$CH(OH)CH_3$ | Threonine |
|  | Proline |
|  | Hydroxyproline |

In addition to naturally occurring amino acid side chain moieties, the amino acid side chain moieties of the present invention also include various derivatives thereof. As used herein, a "derivative" of an amino acid side chain moiety includes modifications and/or variations to naturally occurring amino acid side chain moieties. For example, the amino acid side chain moieties of alanine, valine, leucine, isoleucine and pheylalanine may generally be classified as lower chain alkyl, aryl, or arylalkyl moieties. Derivatives of amino acid side chain moieties include other straight chain or brached, cyclic or noncyclic, substitutes or unsubstituted, saturated or unsaturated lower chain alkyl, aryl or arylalkyl moieties.

As used herein, "lower chain alkyl moieties" contain from 1-12 carbon atoms, "lower chain aryl moieties" contain from 6-12 carbon atoms and "lower chain aralkyl moieties" contain from 7-12 carbon atoms. Thus, in one embodiment, the amino acid side chain derivative is selected from a $C_{1-12}$ alkyl, a $C_{6-12}$ aryl and a $C_{7-12}$ arylalkyl, and in a more preferred embodiment, from a $C_{1-7}$ alkyl, a $C_{6-10}$ aryl and a $C_{7-11}$ arylalkyl.

Amino side chain derivatives of this invention further include substituted derivatives of lower chain alkyl, aryl, and arylalkyl moieties, wherein the substituents is selected from (but are not limited to) one or more of the following chemical moieties: —OH, —OR, —COOH, —COOR, —$CONH_2$, —$NH_2$, —NHR, —NRR, —SH, —SR, —$SO_2R$, —$SO_2H$, —SOR and halogen (including F, Cl, Br and I), wherein each occurrence of R is independently selected from straight chain or branched, cyclic or noncyclic, substituted or unsubstituted, saturated or unsaturated lower chain alkyl, aryl, and aralkyl moieties. Moreover, cyclic lower chain alkyl, aryl and arylalkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of the lower chain alkyl and aralkyl moieties, including (but not limited to) alkyl and aralkyl phosphonates and silanes.

Representative $R_1$, $R_2$, $R_5$, $R_6$, $R_7$, $R_8$ and $R_9$ moieties specifically include (but are not limited to) —OH, —OR, —COR, —COOR, —$CONH_2$, —CONR, —CONRR, —$NH_2$, —NHR, —NRR, —$SO_2R$ and —COSR, wherein each occurrence of R is as defined above.

In a further embodiment, and in addition to being an amino acid side chain moiety or derivative thereof (or the remainder of the compound in the case of $R_1$, $R_2$, $R_5$, $R_6$, $R_7$, $R_8$ and $R_9$), $R_1$, $R_2$, $R_5$, $R_6$, $R_7$, $R_8$ or $R_9$ may be a linker facilitating the linkage of the compound to another moiety or compound. For example, the compounds for use in this invention may be linked to one or more known compounds, such as biotin, for use in diagnostic or screening assay. Furthermore, $R_1$, $R_2$, $R_5$, $R_6$, $R_7$, $R_8$ or $R_9$ may be a linker joining the compound to a solid support (such as a support used in solid phase peptide synthesis) or alternatively, may be the support itself. In this embodiment, linkage to another moiety or compound, or to a solid support, is preferable at the $R_1$, $R_2$, $R_7$ or $R_8$ position, and more preferably at the $R_1$ or $R_2$ position.

In the embodiment wherein A is —(C=O)—CHR$_3$—, B is —N—R$_4$, D is —(C=O)—, E is —(ZR$_6$)—, G is —(C=O)—(XR$_9$)—, the α-helix mimetic compounds for use in this invention have the following general formula (III):

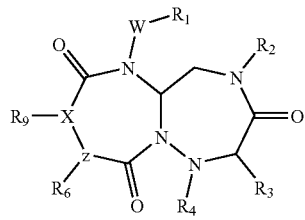

(III)

wherein $R_1$, $R_2$, $R_4$, $R_6$, $R_9$, W and X are as defined above, Z is nitrogen or CH (when Z is CH, then X is nitrogen). In a preferred embodiment, $R_1$, $R_2$, $R_6$, and $R_9$ represent the remainder of the compound, and $R_4$ is selected from an amino acid side chain moiety. In a more specific embodiment wherein A is —O—CHR$_3$—, B is —NR$_4$—, D is —(C=O)—, E is —(ZR$_6$)—, Gi is (XR$_7$)$_n$—, the α-helix mimetic compounds for use in this invention have the following formula (IV):

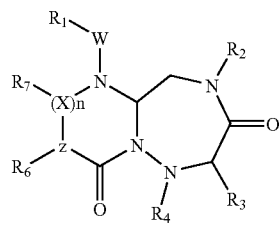

(IV)

wherein $R_1$, $R_2$, $R_4$, $R_6$, $R_7$, W, X and n are as defined above, and Z is nitrogen or CH (when Z is nitrogen, then n is zero, and when Z is CH, then X is nitrogen and n is not zero). In a preferred embodiment, $R_1$, $R_2$, $R_6$, and $R_7$ represent the remainder of the compound, and $R_4$ is selected from an amino acid side chain moiety. In this case, $R_6$ or $R_7$ may be selected from an amino acid side chain moiety when Z and X are CH, respectively.

The α-helix mimetic structures for use in the present invention may be prepared by utilizing appropriate starting component molecules (herinafter referred to as "component pieces"). Briefly, in the synthesis of α-helix mimetic structures having formula (II), first and second component pieces are coupled to form a combined first-second intermediate, if necessary, third and/or fourth component pieces are coupled to form a combined third-fourth intermediate (or, if commercially available, a single third intermediate may be used), the combined first-second intermediate and third-fourth intermediate (or third intermediate) are then coupled to provide a first-second-third-fourth intermediate (or first-second-third intermediate) which is cyclized to yield the α-helix mimetic structures of this invention. Alternatively, the α-helix mimetic structures of formula (II) may be prepared by sequential coupling of the individual component pieces either stepwise in solution or by solid phase synthesis as commonly practiced in solid phase peptide synthesis.

Within the definition above, a "first component piece" has the following formula S1

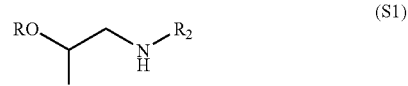

(S1)

Wherein $R_2$ as defined above, and R is a protective group suitable for use in peptide synthesis. Suitable R groups include alkyl groups and, in a preferred embodiment, R is a methyl group. Such first component pieces may be readily synthesized by reductive amination or substitution reaction by displacement of H$_2$N—R$_2$ from CH(OR)$_2$—CHO or CH(OR)$_2$—CH$_2$-Hal (wherein Hal means a halogen atom).

A "second component piece" has the following formula S2:

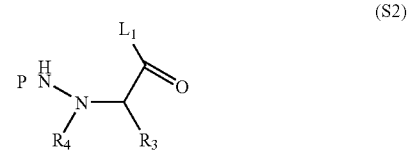

(S2)

Where L1 is carboxyl-activation group such as halogen atom, $R_3$, $R_4$ is as defined above, and P is an amino protective group suitable for use in peptide synthesis. Preferred protective groups include t-butyl dimethylsilyl (TBDMS), t-Butyloxycarbonyl (BOC), Methylosycarbonyl (MOC), 9H-Fluorenylmethyloxycarbonyl (FMOC), and allyloxycarbonyl (Alloc). When L is —C(O)NHR, —NHR may be an carboxyl protective group. N-hydrazino amino acids can be readily prepared according to the procedures of Vidal et al. (Tetrahedron Letters 39:8845-8848, 1998). The conversion of these compounds to the second component pieces of this invention may be readily achieved by activation of the carboxylic acid group of the N-protected hydrazino-amino acid. The conversion of these compounds to the second component pieces may be readily achieved by activation of the carboxylic acid group of the N-protected hydrazino-amino acid. Suitable activated carboxylic acid groups include acid halides where X is a halide such as chloride or bromide, acid anhydrides where X is an acyl group such as acetyl, reactive esters such as an N-hydroxysuccinimide esters and pentafluorophenyl esters, and other activated intermediates such as the active intermediate formed in a coupling reaction using a carbodiimide such as dicyclohexylcarbodiimide (DCC).

15

A "third component piece" has the following formula S3:

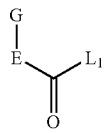
(S3)

where G, E, and $L_1$ are as defined above. Suitable third component pieces are commercially available from a variety of sources or can be prepared by known methods in organic chemistry.

More specifically, the α-helix mimetic structures for use in this invention of formula (II) are synthesized by reacting a first component piece with a second component piece to yield a combined first-second intermediate, followed by either reacting the combined first-second intermediate with third component pieces sequentially to provide a combined first-second-third-fourth intermediate, and the cyclizing this intermediate to yield the α-helix mimetic structure.

The general synthesis of a α-helix having structure I' may be synthesized by the following technique. A first component piece 1 is coupled with a second component piece 2 by using coupling reagent such as phosgene to yield, after N-deprotection, a combined first-second intermediate 1-2 as illustrated below:

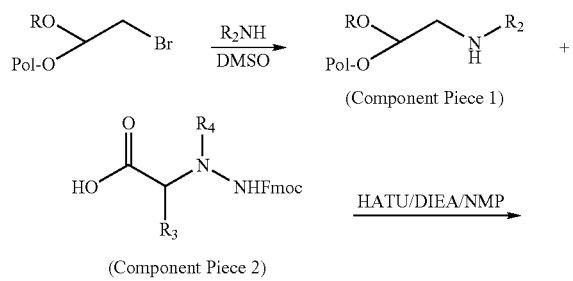

16

-continued

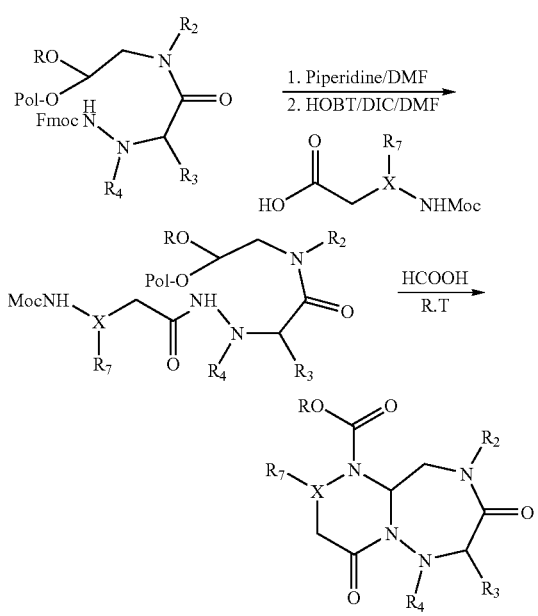

wherein $R_1$, $R_2$, $R_4$, $R_7$.Fmoc, Moc and X are as defined above, and Pol represents a polymeric support.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and for that various modifications or changes in light thereof will be suggested to persons skilled in the art and are to be included within the spirit and purview of this application.

---

What is claimed is:

1. A method for modulating the interaction of gamma-catenin with p300 in a stem cell or a progenitor cell, comprising treating said cell ex vivo with an agent that modulates a post-translational modifications of p300 or but does not directly bind to p300.

2. The method of claim 1 wherein the agent decreases the binding of p300 to gamma-catenin.

3. The method of claim 1 wherein the agent increases the binding of p300 to gamma-catenin.

4. The method of claim 1 wherein the agent decreases the binding of gamma-catenin to the amino-terminal 110 amino acids of p300.

5. The method of claim 1 wherein the agent inhibits phosphorylation of Ser89 of p300.

6. The method of claim 5 wherein said agent is an analog of Fusicoccin.

7. The method of claim 1 wherein the agent is incorporated into a biomaterial capable of supporting the growth of a stem cell.

8. The method of claim 1, wherein the agent is a compound having the following general formula (I):

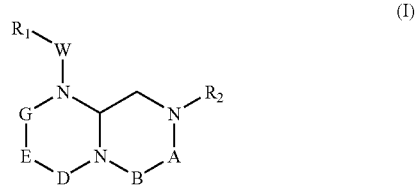

wherein A is —(CHR$_3$)—(C=O)—, B is —(NR$_4$)—, D is —(CHR$_5$)— or —(C=O)—, E is —(ZR$_6$)—, —(C=O)—, G is —(XR$_7$)$_n$—, —(CHR$_7$)—(NR$_8$)—, —(C=O)—(XR$_9$)—, or —(C=O)—, W is —Y(C=O)—, —(C=O)NH—, —(SO$_2$)— or nothing, Y is oxygen or sulfur, X and Z is independently nitrogen or CH, n=0 or 1, R$_2$ is selected from a monocyclic aryl or heteroaryl moiety bearing the substituent NR$_{10}$R$_{11}$, and R$_1$, R$_3$, R$_4$, R$_5$, R$_6$, R$_7$, R$_8$, R$_9$, R$_{10}$, and R$_{11}$ are the same or different and independently selected from an amino acid side chain moiety or derivative thereof, a linker and a solid support.

* * * * *

UNITED STATES PATENT AND TRADEMARK OFFICE
CERTIFICATE OF CORRECTION

PATENT NO. : 7,563,825 B1　　　　　　　　　　　　　　　　　　　　　　　　Page 1 of 1
APPLICATION NO. : 11/377898
DATED : July 21, 2009
INVENTOR(S) : Michael Kahn It is certified that error appears in the above-identified patent and that said Letters Patent is hereby corrected as shown below:

Title Page, Item (56) Other Publications:
"Rebel, V. et al., "Amplification of Sca-1 $^+$ Lin $^-$WGA $^+$ Cells in Serum-Free Cultures Containing Stell Factor" should read, --Rebel, V. et al., "Amplification of Sca-1 $^+$ Lin $^-$WGA $^+$ Cells in Serum-Free Cultures Containing Steel Factor--.

Column 47
Line 30, "post-translational modifications of p300 or but does not" should read, --post-translational modification of p300 or gamma-catenin but does not--.

Signed and Sealed this

Twenty-eighth Day of September, 2010

David J. Kappos
*Director of the United States Patent and Trademark Office*

SEQUENCE LISTING

<160> NUMBER OF SEQ ID NOS: 4

<210> SEQ ID NO 1
<211> LENGTH: 2440
<212> TYPE: PRT
<213> ORGANISM: Homo sapiens

<400> SEQUENCE: 1

```
Met Ala Glu Asn Leu Leu Asp Gly Pro Pro Asn Pro Lys Arg Ala Lys
1               5                   10                  15

Leu Ser Ser Pro Gly Phe Ser Ala Asn Ser Asn Thr Asp Phe Gly Ser
            20                  25                  30

Leu Phe Asp Leu Glu Asn Asp Leu Pro Asp Glu Leu Ile Pro Asn Gly
        35                  40                  45

Gly Glu Leu Gly Leu Leu Asn Ser Gly Asn Leu Val Pro Asp Ala Ala
    50                  55                  60

Ser Lys His Lys Gln Leu Ser Glu Leu Leu Arg Gly Gly Ser Gly Ser
65                  70                  75                  80
```

```
Ser Ile Asn Pro Gly Ile Gly Asn Val Ser Ala Ser Ser Pro Val Gln
                85                  90                  95
Gln Gly Leu Gly Gly Gln Ala Gln Gly Gln Pro Asn Ser Ala Asn Met
            100                 105                 110
Ala Ser Leu Ser Ala Met Gly Lys Ser Pro Leu Ser Gln Gly Asp Ser
        115                 120                 125
Ser Ser Pro Ser Leu Pro Lys Gln Ala Ser Thr Ser Gly Pro Thr
    130                 135                 140
Pro Ala Ala Ser Gln Ala Leu Asn Pro Gln Ala Gln Lys Gln Val Gly
145                 150                 155                 160
Leu Ala Thr Ser Ser Pro Ala Thr Ser Gln Thr Gly Pro Gly Ile Cys
                165                 170                 175
Met Asn Ala Asn Phe Asn Gln Thr His Pro Gly Leu Leu Asn Ser Asn
            180                 185                 190
Ser Gly His Ser Leu Ile Asn Gln Ala Ser Gln Gly Gln Ala Gln Val
        195                 200                 205
Met Asn Gly Ser Leu Gly Ala Ala Gly Arg Gly Arg Gly Ala Gly Met
    210                 215                 220
Pro Tyr Thr Ala Pro Ala Met Gln Gly Ala Ser Ser Ser Val Leu Ala
225                 230                 235                 240
Glu Thr Leu Thr Gln Val Ser Pro Gln Thr Ala Gly His Ala Gly Leu
                245                 250                 255
Asn Thr Ala Gln Ala Gly Gly Met Ala Lys Ile Gly Met Asn Gly Thr
            260                 265                 270
Thr Ser Pro Phe Gly Gln Pro Phe Ser Gln Ala Gly Gly Gln Pro Met
        275                 280                 285
Gly Ala Thr Gly Val Asn Pro Gln Leu Ala Ser Lys Gln Ser Met Val
    290                 295                 300
Asn Ser Leu Pro Thr Phe Pro Thr Asp Ile Lys Asn Thr Ser Val Thr
305                 310                 315                 320
Asn Val Pro Asn Met Ser Gln Met Gln Thr Ser Val Gly Ile Val Pro
                325                 330                 335
Thr Gln Ala Ile Ala Thr Gly Pro Thr Ala Asp Pro Glu Lys Arg Lys
            340                 345                 350
Leu Ile Gln Gln Gln Leu Val Leu Leu Leu His Ala His Lys Cys Gln
        355                 360                 365
Arg Arg Glu Gln Ala Asn Gly Glu Val Arg Ala Cys Ser Leu Pro His
    370                 375                 380
Cys Arg Thr Met Lys Asn Val Leu Asn His Met Thr His Cys Gln Ala
385                 390                 395                 400
Gly Lys Ala Cys Gln Val Ala His Cys Ala Ser Ser Arg Gln Ile Ile
                405                 410                 415
Ser His Trp Lys Asn Cys Thr Arg His Asp Cys Pro Val Cys Leu Pro
            420                 425                 430
Leu Lys Asn Ala Ser Asp Lys Arg Asn Gln Gln Thr Ile Leu Gly Ser
        435                 440                 445
Pro Ala Ser Gly Ile Gln Asn Thr Ile Gly Ser Val Gly Thr Gly Gln
    450                 455                 460
Gln Asn Ala Thr Ser Leu Ser Asn Pro Asn Pro Ile Asp Pro Ser Ser
465                 470                 475                 480
Met Gln Arg Ala Tyr Ala Ala Leu Gly Leu Pro Tyr Met Asn Gln Pro
                485                 490                 495
```

```
-continued

Gln Thr Gln Leu Gln Pro Gln Val Pro Gly Gln Gln Pro Ala Gln Pro
            500                 505                 510

Gln Thr His Gln Gln Met Arg Thr Leu Asn Pro Leu Gly Asn Asn Pro
            515                 520                 525

Met Asn Ile Pro Ala Gly Gly Ile Thr Thr Asp Gln Gln Pro Pro Asn
            530                 535                 540

Leu Ile Ser Glu Ser Ala Leu Pro Thr Ser Leu Gly Ala Thr Asn Pro
545                 550                 555                 560

Leu Met Asn Asp Gly Ser Asn Ser Gly Asn Ile Gly Thr Leu Ser Thr
                565                 570                 575

Ile Pro Thr Ala Ala Pro Pro Ser Ser Thr Gly Val Arg Lys Gly Trp
            580                 585                 590

His Glu His Val Thr Gln Asp Leu Arg Ser His Leu Val His Lys Leu
            595                 600                 605

Val Gln Ala Ile Phe Pro Thr Pro Asp Pro Ala Ala Leu Lys Asp Arg
            610                 615                 620

Arg Met Glu Asn Leu Val Ala Tyr Ala Lys Lys Val Glu Gly Asp Met
625                 630                 635                 640

Tyr Glu Ser Ala Asn Ser Arg Asp Glu Tyr Tyr His Leu Leu Ala Glu
                645                 650                 655

Lys Ile Tyr Lys Ile Gln Lys Glu Leu Glu Glu Lys Arg Arg Ser Arg
            660                 665                 670

Leu His Lys Gln Gly Ile Leu Gly Asn Gln Pro Ala Leu Pro Ala Pro
            675                 680                 685

Gly Ala Gln Pro Pro Val Ile Pro Gln Ala Gln Ser Val Arg Pro Pro
            690                 695                 700

Asn Gly Pro Leu Ser Leu Pro Val Asn Arg Met Gln Val Ser Gln Gly
705                 710                 715                 720

Met Asn Ser Phe Asn Pro Met Ser Leu Gly Asn Val Gln Leu Pro Gln
                725                 730                 735

Ala Pro Met Gly Pro Arg Ala Ala Ser Pro Met Asn His Ser Val Gln
            740                 745                 750

Met Asn Ser Met Gly Ser Val Pro Gly Met Ala Ile Ser Pro Ser Arg
            755                 760                 765

Met Pro Gln Pro Pro Asn Met Met Gly Ala His Thr Asn Asn Met Met
            770                 775                 780

Ala Gln Ala Pro Ala Gln Ser Gln Phe Leu Pro Gln Asn Gln Phe Pro
785                 790                 795                 800

Ser Ser Ser Gly Ala Met Ser Val Gly Met Gly Gln Pro Pro Ala Gln
                805                 810                 815

Thr Gly Val Ser Gln Gly Gln Val Pro Gly Ala Ala Leu Pro Asn Pro
            820                 825                 830

Leu Asn Met Leu Gly Pro Gln Ala Ser Gln Leu Pro Cys Pro Pro Val
            835                 840                 845

Thr Gln Ser Pro Leu His Pro Thr Pro Pro Ala Ser Thr Ala Ala
            850                 855                 860

Gly Met Pro Ser Leu Gln His Thr Thr Pro Pro Gly Met Thr Pro Pro
865                 870                 875                 880

Gln Pro Ala Ala Pro Thr Gln Pro Ser Thr Pro Val Ser Ser Ser Gly
                885                 890                 895

Gln Thr Pro Thr Pro Thr Pro Gly Ser Val Pro Ser Ala Thr Gln Thr
            900                 905                 910

Gln Ser Thr Pro Thr Val Gln Ala Ala Ala Gln Ala Gln Val Thr Pro
```

-continued

```
                915                 920                 925
Gln Pro Gln Thr Pro Val Gln Pro Pro Ser Val Ala Thr Pro Gln Ser
            930                 935                 940
Ser Gln Gln Gln Pro Thr Pro Val His Ala Gln Pro Pro Gly Thr Pro
945                 950                 955                 960
Leu Ser Gln Ala Ala Ala Ser Ile Asp Asn Arg Val Pro Thr Pro Ser
                965                 970                 975
Thr Val Ala Ser Ala Glu Thr Asn Ser Gln Gln Pro Gly Pro Asp Val
            980                 985                 990
Pro Val Leu Glu Met Lys Thr Glu Thr Gln Ala Glu Asp Thr Glu Pro
            995                 1000                1005
Asp Pro Gly Glu Ser Lys Gly Glu Pro Arg Ser Glu Met Met Glu Glu
            1010                1015                1020
Asp Leu Gln Gly Ala Ser Gln Val Lys Glu Glu Thr Asp Ile Ala Glu
1025                1030                1035                1040
Gln Lys Ser Glu Pro Met Glu Val Glu Asp Lys Lys Pro Glu Val Lys
                1045                1050                1055
Val Glu Val Lys Glu Glu Glu Ser Ser Ser Asn Gly Thr Ala Ser
            1060                1065                1070
Gln Ser Thr Ser Pro Ser Gln Pro Arg Lys Lys Ile Phe Lys Pro Glu
            1075                1080                1085
Glu Leu Arg Gln Ala Leu Met Pro Thr Leu Glu Ala Leu Tyr Arg Gln
            1090                1095                1100
Asp Pro Glu Ser Leu Pro Phe Arg Gln Pro Val Asp Pro Gln Leu Leu
1105                1110                1115                1120
Gly Ile Pro Asp Tyr Phe Asp Ile Val Lys Asn Pro Met Asp Leu Ser
                1125                1130                1135
Thr Ile Lys Arg Lys Leu Asp Thr Gly Gln Tyr Gln Glu Pro Trp Gln
            1140                1145                1150
Tyr Val Asp Asp Val Trp Leu Met Phe Asn Asn Ala Trp Leu Tyr Asn
                1155                1160                1165
Arg Lys Thr Ser Arg Val Tyr Lys Phe Cys Ser Lys Leu Ala Glu Val
            1170                1175                1180
Phe Glu Gln Glu Ile Asp Pro Val Met Gln Ser Leu Gly Tyr Cys Cys
1185                1190                1195                1200
Gly Arg Lys Tyr Glu Phe Ser Pro Gln Thr Leu Cys Cys Tyr Gly Lys
                1205                1210                1215
Gln Leu Cys Thr Ile Pro Arg Asp Ala Ala Tyr Tyr Ser Tyr Gln Asn
            1220                1225                1230
Arg Tyr His Phe Cys Glu Lys Cys Phe Thr Glu Ile Gln Gly Glu Asn
            1235                1240                1245
Val Thr Leu Gly Asp Asp Pro Ser Gln Pro Gln Thr Thr Ile Ser Lys
            1250                1255                1260
Asp Gln Phe Glu Lys Lys Lys Asn Asp Thr Leu Asp Pro Glu Pro Phe
1265                1270                1275                1280
Val Asp Cys Lys Glu Cys Gly Arg Lys Met His Gln Ile Cys Val Leu
                1285                1290                1295
His Tyr Asp Ile Ile Trp Pro Ser Gly Phe Val Cys Asp Asn Cys Leu
            1300                1305                1310
Lys Lys Thr Gly Arg Pro Arg Lys Glu Asn Lys Phe Ser Ala Lys Arg
            1315                1320                1325
Leu Gln Thr Thr Arg Leu Gly Asn His Leu Glu Asp Arg Val Asn Lys
            1330                1335                1340
```

-continued

```
Phe Leu Arg Arg Gln Asn His Pro Glu Ala Gly Glu Val Phe Val Arg
1345                1350                1355                1360

Val Val Ala Ser Ser Asp Lys Thr Val Glu Val Lys Pro Gly Met Lys
            1365                1370                1375

Ser Arg Phe Val Asp Ser Gly Glu Met Ser Glu Ser Phe Pro Tyr Arg
            1380                1385                1390

Thr Lys Ala Leu Phe Ala Phe Glu Glu Ile Asp Gly Val Asp Val Cys
            1395                1400                1405

Phe Phe Gly Met His Val Gln Asp Thr Ala Leu Ile Ala Pro His Gln
        1410                1415                1420

Ile Gln Gly Cys Val Tyr Ile Ser Tyr Leu Asp Ser Ile His Phe Phe
1425                1430                1435                1440

Arg Pro Arg Cys Leu Arg Thr Ala Val Tyr His Glu Ile Leu Ile Gly
            1445                1450                1455

Tyr Leu Glu Tyr Val Lys Lys Leu Val Tyr Val Thr Ala His Ile Trp
            1460                1465                1470

Ala Cys Pro Pro Ser Glu Gly Asp Asp Tyr Ile Phe His Cys His Pro
            1475                1480                1485

Pro Asp Gln Lys Ile Pro Lys Pro Lys Arg Leu Gln Glu Trp Tyr Lys
            1490                1495                1500

Lys Met Leu Asp Lys Ala Phe Ala Glu Arg Ile Ile Asn Asp Tyr Lys
1505                1510                1515                1520

Asp Ile Phe Lys Gln Ala Asn Glu Asp Arg Leu Thr Ser Ala Lys Glu
            1525                1530                1535

Leu Pro Tyr Phe Glu Gly Asp Phe Trp Pro Asn Val Leu Glu Glu Ser
            1540                1545                1550

Ile Lys Glu Leu Glu Gln Glu Glu Glu Arg Lys Lys Glu Glu Ser
            1555                1560                1565

Thr Ala Ala Ser Glu Thr Pro Glu Gly Ser Gln Gly Asp Ser Lys Asn
            1570                1575                1580

Ala Lys Lys Lys Asn Asn Lys Lys Thr Asn Lys Asn Lys Ser Ser Ile
1585                1590                1595                1600

Ser Arg Ala Asn Lys Lys Lys Pro Ser Met Pro Asn Val Ser Asn Asp
            1605                1610                1615

Leu Ser Gln Lys Leu Tyr Ala Thr Met Glu Lys His Lys Glu Val Phe
            1620                1625                1630

Phe Val Ile His Leu His Ala Gly Pro Val Ile Ser Thr Gln Pro Pro
            1635                1640                1645

Ile Val Asp Pro Asp Pro Leu Leu Ser Cys Asp Leu Met Asp Gly Arg
            1650                1655                1660

Asp Ala Phe Leu Thr Leu Ala Arg Asp Lys His Trp Glu Phe Ser Ser
1665                1670                1675                1680

Leu Arg Arg Ser Lys Trp Ser Thr Leu Cys Met Leu Val Glu Leu His
            1685                1690                1695

Thr Gln Gly Gln Asp Arg Phe Val Tyr Thr Cys Asn Glu Cys Lys His
            1700                1705                1710

His Val Glu Thr Arg Trp His Cys Thr Val Cys Glu Asp Tyr Asp Leu
            1715                1720                1725

Cys Ile Asn Cys Tyr Asn Thr Lys Ser His Thr His Lys Met Val Lys
            1730                1735                1740

Trp Gly Leu Gly Leu Asp Asp Glu Gly Ser Ser Gln Gly Glu Pro Gln
1745                1750                1755                1760
```

-continued

```
Ser Lys Ser Pro Gln Glu Ser Arg Arg Leu Ser Ile Gln Arg Cys Ile
            1765                1770                1775

Gln Ser Leu Val His Ala Cys Gln Cys Arg Asn Ala Asn Cys Ser Leu
        1780                1785                1790

Pro Ser Cys Gln Lys Met Lys Arg Val Val Gln His Thr Lys Gly Cys
    1795                1800                1805

Lys Arg Lys Thr Asn Gly Gly Cys Pro Val Cys Lys Gln Leu Ile Ala
1810                1815                1820

Leu Cys Cys Tyr His Ala Lys His Cys Gln Glu Asn Lys Cys Pro Val
1825                1830                1835                1840

Pro Phe Cys Leu Asn Ile Lys His Asn Val Arg Gln Gln Ile Gln
            1845                1850                1855

His Cys Leu Gln Gln Ala Gln Leu Met Arg Arg Arg Met Ala Thr Met
        1860                1865                1870

Asn Thr Arg Asn Val Pro Gln Gln Ser Leu Pro Ser Pro Thr Ser Ala
    1875                1880                1885

Pro Pro Gly Thr Pro Thr Gln Gln Pro Ser Thr Pro Gln Thr Pro Gln
1890                1895                1900

Pro Pro Ala Gln Pro Gln Pro Ser Pro Val Asn Met Ser Pro Ala Gly
1905                1910                1915                1920

Phe Pro Asn Val Ala Arg Thr Gln Pro Thr Ile Val Ser Ala Gly
            1925                1930                1935

Lys Pro Thr Asn Gln Val Pro Ala Pro Pro Pro Ala Gln Pro Pro
        1940                1945                1950

Pro Ala Ala Val Glu Ala Ala Arg Gln Ile Glu Arg Glu Ala Gln Gln
    1955                1960                1965

Gln Gln His Leu Tyr Arg Ala Asn Ile Asn Asn Gly Met Pro Pro Gly
    1970                1975                1980

Arg Asp Gly Met Gly Thr Pro Gly Ser Gln Met Thr Pro Val Gly Leu
1985                1990                1995                2000

Asn Val Pro Arg Pro Asn Gln Val Ser Gly Pro Val Met Ser Ser Met
            2005                2010                2015

Pro Pro Gly Gln Trp Gln Gln Ala Pro Ile Pro Gln Gln Pro Met
        2020                2025                2030

Pro Gly Met Pro Arg Pro Val Met Ser Met Gln Ala Gln Ala Ala Val
    2035                2040                2045

Ala Gly Pro Arg Met Pro Asn Val Gln Pro Asn Arg Ser Ile Ser Pro
    2050                2055                2060

Ser Ala Leu Gln Asp Leu Leu Arg Thr Leu Lys Ser Pro Ser Ser Pro
2065                2070                2075                2080

Gln Gln Gln Gln Gln Val Leu Asn Ile Leu Lys Ser Asn Pro Gln Leu
            2085                2090                2095

Met Ala Ala Phe Ile Lys Gln Arg Thr Ala Lys Tyr Val Ala Asn Gln
        2100                2105                2110

Pro Gly Met Gln Pro Gln Pro Gly Leu Gln Ser Gln Pro Gly Met Gln
    2115                2120                2125

Pro Gln Pro Gly Met His Gln Gln Pro Ser Leu Gln Asn Leu Asn Ala
    2130                2135                2140

Met Gln Ala Gly Val Pro Arg Pro Gly Val Pro Pro Gln Pro Ala
2145                2150                2155                2160

Met Gly Gly Leu Asn Pro Gln Gly Gln Ala Leu Asn Ile Met Asn Pro
            2165                2170                2175

Gly His Asn Pro Asn Met Thr Asn Met Asn Pro Gln Tyr Arg Glu Met
```

-continued

```
                2180                2185                2190
Val Arg Arg Gln Leu Leu Gln His Gln Gln Gln Gln Gln Gln Gln Gln
            2195                2200                2205
Gln Gln Gln Gln Gln Gln Asn Ser Ala Ser Leu Ala Gly Gly Met
        2210                2215                2220
Ala Gly His Ser Gln Phe Gln Pro Gln Gly Pro Gly Gly Tyr Ala
2225                2230                2235                2240
Pro Ala Met Gln Gln Arg Met Gln Gln His Leu Pro Ile Gln Gly
                2245                2250                2255
Ser Ser Met Gly Gln Met Ala Ala Pro Met Gly Gln Leu Gly Gln Met
            2260                2265                2270
Gly Gln Pro Gly Leu Gly Ala Asp Ser Thr Pro Asn Ile Gln Gln Ala
        2275                2280                2285
Leu Gln Gln Arg Ile Leu Gln Gln Gln Met Lys Gln Gln Ile Gly
            2290                2295                2300
Ser Pro Gly Gln Pro Asn Pro Met Ser Pro Gln His Met Leu Ser
2305                2310                2315                2320
Gly Gln Pro Gln Ala Ser His Leu Pro Gly Gln Gln Ile Ala Thr Ser
            2325                2330                2335
Leu Ser Asn Gln Val Arg Ser Pro Ala Pro Val Gln Ser Pro Arg Pro
        2340                2345                2350
Gln Ser Gln Pro Pro His Ser Ser Pro Ser Pro Arg Ile Gln Pro Gln
            2355                2360                2365
Pro Ser Pro His His Val Ser Pro Gln Thr Gly Thr Pro His Pro Gly
        2370                2375                2380
Leu Ala Val Thr Met Ala Ser Ser Met Asp Gln Gly His Leu Gly Asn
2385                2390                2395                2400
Pro Glu Gln Ser Ala Met Leu Pro Gln Leu Asn Thr Pro Asn Arg Ser
            2405                2410                2415
Ala Leu Ser Ser Glu Leu Ser Leu Val Gly Asp Thr Thr Gly Asp Thr
        2420                2425                2430
Leu Glu Lys Phe Val Glu Gly Leu
        2435                2440

<210> SEQ ID NO 2
<211> LENGTH: 2414
<212> TYPE: PRT
<213> ORGANISM: Homo sapiens

<400> SEQUENCE: 2

Met Ala Glu Asn Val Val Glu Pro Gly Pro Pro Ser Ala Lys Arg Pro
  1               5                  10                  15
Lys Leu Ser Ser Pro Ala Leu Ser Ala Ser Ala Ser Asp Gly Thr Asp
            20                  25                  30
Phe Gly Ser Leu Phe Asp Leu Glu His Asp Leu Pro Asp Glu Leu Ile
        35                  40                  45
Asn Ser Thr Glu Leu Gly Leu Thr Asn Gly Gly Asp Ile Asn Gln Leu
    50                  55                  60
Gln Thr Ser Leu Gly Met Val Gln Asp Ala Ala Ser Lys His Lys Gln
65                  70                  75                  80
Leu Ser Glu Leu Leu Arg Ser Gly Ser Ser Pro Asn Leu Asn Met Gly
                85                  90                  95
Val Gly Gly Pro Gly Gln Val Met Ala Ser Gln Ala Gln Gln Ser Ser
            100                 105                 110
```

-continued

```
Pro Gly Leu Gly Leu Ile Asn Ser Met Val Lys Ser Pro Met Thr Gln
            115                 120                 125

Ala Gly Leu Thr Ser Pro Asn Met Gly Met Gly Thr Ser Gly Pro Asn
        130                 135                 140

Gln Gly Pro Thr Gln Ser Thr Gly Met Met Asn Ser Pro Val Asn Gln
145                 150                 155                 160

Pro Ala Met Gly Met Asn Thr Gly Thr Asn Ala Gly Met Asn Pro Gly
                165                 170                 175

Met Leu Ala Ala Gly Asn Gly Gln Gly Ile Met Pro Asn Gln Val Met
            180                 185                 190

Asn Gly Ser Ile Gly Ala Gly Arg Gly Arg Gln Asp Met Gln Tyr Pro
        195                 200                 205

Asn Pro Gly Met Gly Ser Ala Gly Asn Leu Leu Thr Glu Pro Leu Gln
    210                 215                 220

Gln Gly Ser Pro Gln Met Gly Gly Gln Thr Gly Leu Arg Gly Pro Gln
225                 230                 235                 240

Pro Leu Lys Met Gly Met Met Asn Asn Pro Asn Pro Tyr Gly Ser Pro
                245                 250                 255

Tyr Thr Gln Asn Pro Gly Gln Gln Ile Gly Ala Ser Gly Leu Gly Leu
            260                 265                 270

Gln Ile Gln Thr Lys Thr Val Leu Ser Asn Asn Leu Ser Pro Phe Ala
        275                 280                 285

Met Asp Lys Lys Ala Val Pro Gly Gly Met Pro Asn Met Gly Gln
    290                 295                 300

Gln Pro Ala Pro Gln Val Gln Gln Pro Gly Leu Val Thr Pro Val Ala
305                 310                 315                 320

Gln Gly Met Gly Ser Gly Ala His Thr Ala Asp Pro Glu Lys Arg Lys
                325                 330                 335

Leu Ile Gln Gln Gln Leu Val Leu Leu Leu His Ala His Lys Cys Gln
            340                 345                 350

Arg Arg Glu Gln Ala Asn Gly Glu Val Arg Gln Cys Asn Leu Pro His
        355                 360                 365

Cys Arg Thr Met Lys Asn Val Leu Asn His Met Thr His Cys Gln Ser
    370                 375                 380

Gly Lys Ser Cys Gln Val Ala His Cys Ala Ser Ser Arg Gln Ile Ile
385                 390                 395                 400

Ser His Trp Lys Asn Cys Thr Arg His Asp Cys Pro Val Cys Leu Pro
                405                 410                 415

Leu Lys Asn Ala Gly Asp Lys Arg Asn Gln Gln Pro Ile Leu Thr Gly
            420                 425                 430

Ala Pro Val Gly Leu Gly Asn Pro Ser Ser Leu Gly Val Gly Gln Gln
        435                 440                 445

Ser Ala Pro Asn Leu Ser Thr Val Ser Gln Ile Asp Pro Ser Ser Ile
    450                 455                 460

Glu Arg Ala Tyr Ala Ala Leu Gly Leu Pro Tyr Gln Val Asn Gln Met
465                 470                 475                 480

Pro Thr Gln Pro Gln Val Gln Ala Lys Asn Gln Asn Gln Gln Pro
                485                 490                 495

Gly Gln Ser Pro Gln Gly Met Arg Pro Met Ser Asn Met Ser Ala Ser
            500                 505                 510

Pro Met Gly Val Asn Gly Gly Val Gly Val Gln Thr Pro Ser Leu Leu
        515                 520                 525

Ser Asp Ser Met Leu His Ser Ala Ile Asn Ser Gln Asn Pro Met Met
```

```
                530                 535                 540
Ser Glu Asn Ala Ser Val Pro Ser Leu Gly Pro Met Pro Thr Ala Ala
545                 550                 555                 560

Gln Pro Ser Thr Thr Gly Ile Arg Lys Gln Trp His Glu Asp Ile Thr
                565                 570                 575

Gln Asp Leu Arg Asn His Leu Val His Lys Leu Val Gln Ala Ile Phe
                580                 585                 590

Pro Thr Pro Asp Pro Ala Ala Leu Lys Asp Arg Arg Met Glu Asn Leu
                595                 600                 605

Val Ala Tyr Ala Arg Lys Val Glu Gly Asp Met Tyr Glu Ser Ala Asn
                610                 615                 620

Asn Arg Ala Glu Tyr Tyr His Leu Leu Ala Glu Lys Ile Tyr Lys Ile
625                 630                 635                 640

Gln Lys Glu Leu Glu Glu Lys Arg Arg Thr Arg Leu Gln Lys Gln Asn
                645                 650                 655

Met Leu Pro Asn Ala Ala Gly Met Val Pro Val Ser Met Asn Pro Gly
                660                 665                 670

Pro Asn Met Gly Gln Pro Gln Pro Gly Met Thr Ser Asn Gly Pro Leu
                675                 680                 685

Pro Asp Pro Ser Met Ile Arg Gly Ser Val Pro Asn Gln Met Met Pro
                690                 695                 700

Arg Ile Thr Pro Gln Ser Gly Leu Asn Gln Phe Gly Gln Met Ser Met
705                 710                 715                 720

Ala Gln Pro Pro Ile Val Pro Arg Gln Thr Pro Pro Leu Gln His His
                725                 730                 735

Gly Gln Leu Ala Gln Pro Gly Ala Leu Asn Pro Pro Met Gly Tyr Gly
                740                 745                 750

Pro Arg Met Gln Gln Pro Ser Asn Gln Gly Gln Phe Leu Pro Gln Thr
                755                 760                 765

Gln Phe Pro Ser Gln Gly Met Asn Val Thr Asn Ile Pro Leu Ala Pro
                770                 775                 780

Ser Ser Gly Gln Ala Pro Val Ser Gln Ala Gln Met Ser Ser Ser Ser
785                 790                 795                 800

Cys Pro Val Asn Ser Pro Ile Met Pro Pro Gly Ser Gln Gly Ser His
                805                 810                 815

Ile His Cys Pro Gln Leu Pro Gln Pro Ala Leu His Gln Asn Ser Pro
                820                 825                 830

Ser Pro Val Pro Ser Arg Thr Pro Thr Pro His His Thr Pro Pro Ser
                835                 840                 845

Ile Gly Ala Gln Gln Pro Pro Ala Thr Thr Ile Pro Ala Pro Val Pro
850                 855                 860

Thr Pro Pro Ala Met Pro Pro Gly Pro Gln Ser Gln Ala Leu His Pro
865                 870                 875                 880

Pro Pro Arg Gln Thr Pro Thr Pro Pro Thr Thr Gln Leu Pro Gln Gln
                885                 890                 895

Val Gln Pro Ser Leu Pro Ala Ala Pro Ser Ala Asp Gln Pro Gln Gln
                900                 905                 910

Gln Pro Arg Ser Gln Gln Ser Thr Ala Ala Ser Val Pro Thr Pro Asn
                915                 920                 925

Ala Pro Leu Leu Pro Pro Gln Pro Ala Thr Pro Leu Ser Gln Pro Ala
                930                 935                 940

Val Ser Ile Glu Gly Gln Val Ser Asn Pro Pro Ser Thr Ser Ser Thr
945                 950                 955                 960
```

-continued

```
Glu Val Asn Ser Gln Ala Ile Ala Glu Lys Gln Pro Ser Gln Glu Val
                965                 970                 975
Lys Met Glu Ala Lys Met Glu Val Asp Gln Pro Glu Pro Ala Asp Thr
            980                 985                 990
Gln Pro Glu Asp Ile Ser Glu Ser Lys Val Glu Asp Cys Lys Met Glu
        995                1000                1005
Ser Thr Glu Thr Glu Glu Arg Ser Thr Glu Leu Lys Thr Glu Ile Lys
       1010                1015                1020
Glu Glu Glu Asp Gln Pro Ser Thr Ser Ala Thr Gln Ser Ser Pro Ala
1025                1030                1035                1040
Pro Gly Gln Ser Lys Lys Lys Ile Phe Lys Pro Glu Glu Leu Arg Gln
                1045                1050                1055
Ala Leu Met Pro Thr Leu Glu Ala Leu Tyr Arg Gln Asp Pro Glu Ser
            1060                1065                1070
Leu Pro Phe Arg Gln Pro Val Asp Pro Gln Leu Leu Gly Ile Pro Asp
        1075                1080                1085
Tyr Phe Asp Ile Val Lys Ser Pro Met Asp Leu Ser Thr Ile Lys Arg
       1090                1095                1100
Lys Leu Asp Thr Gly Gln Tyr Gln Glu Pro Trp Gln Tyr Val Asp Asp
1105                1110                1115                1120
Ile Trp Leu Met Phe Asn Asn Ala Trp Leu Tyr Asn Arg Lys Thr Ser
                1125                1130                1135
Arg Val Tyr Lys Tyr Cys Ser Lys Leu Ser Glu Val Phe Glu Gln Glu
            1140                1145                1150
Ile Asp Pro Val Met Gln Ser Leu Gly Tyr Cys Cys Gly Arg Lys Leu
        1155                1160                1165
Glu Phe Ser Pro Gln Thr Leu Cys Cys Tyr Gly Lys Gln Leu Cys Thr
       1170                1175                1180
Ile Pro Arg Asp Ala Thr Tyr Tyr Ser Tyr Gln Asn Arg Tyr His Phe
1185                1190                1195                1200
Cys Glu Lys Cys Phe Asn Glu Ile Gln Gly Glu Ser Val Ser Leu Gly
                1205                1210                1215
Asp Asp Pro Ser Gln Pro Gln Thr Thr Ile Asn Lys Glu Gln Phe Ser
            1220                1225                1230
Lys Arg Lys Asn Asp Thr Leu Asp Pro Glu Leu Phe Val Glu Cys Thr
        1235                1240                1245
Glu Cys Gly Arg Lys Met His Gln Ile Cys Val Leu His His Glu Ile
       1250                1255                1260
Ile Trp Pro Ala Gly Phe Val Cys Asp Gly Cys Leu Lys Lys Ser Ala
1265                1270                1275                1280
Arg Thr Arg Lys Glu Asn Lys Phe Ser Ala Lys Arg Leu Pro Ser Thr
                1285                1290                1295
Arg Leu Gly Thr Phe Leu Glu Asn Arg Val Asn Asp Phe Leu Arg Arg
            1300                1305                1310
Gln Asn His Pro Glu Ser Gly Glu Val Thr Val Arg Val Val His Ala
        1315                1320                1325
Ser Asp Lys Thr Val Glu Val Lys Pro Gly Met Lys Ala Arg Phe Val
       1330                1335                1340
Asp Ser Gly Glu Met Ala Glu Ser Phe Pro Tyr Arg Thr Lys Ala Leu
1345                1350                1355                1360
Phe Ala Phe Glu Glu Ile Asp Gly Val Asp Leu Cys Phe Phe Gly Met
                1365                1370                1375
```

-continued

His Val Gln Glu Tyr Gly Ser Asp Cys Pro Pro Asn Gln Arg Arg
            1380                1385                1390

Val Tyr Ile Ser Tyr Leu Asp Ser Val His Phe Phe Arg Pro Lys Cys
            1395                1400                1405

Leu Arg Thr Ala Val Tyr His Glu Ile Leu Ile Gly Tyr Leu Glu Tyr
            1410                1415                1420

Val Lys Lys Leu Gly Tyr Thr Thr Gly His Ile Trp Ala Cys Pro Pro
1425                1430                1435                1440

Ser Glu Gly Asp Asp Tyr Ile Phe His Cys His Pro Pro Asp Gln Lys
            1445                1450                1455

Ile Pro Lys Pro Lys Arg Leu Gln Glu Trp Tyr Lys Lys Met Leu Asp
            1460                1465                1470

Lys Ala Val Ser Glu Arg Ile Val His Asp Tyr Lys Asp Ile Phe Lys
            1475                1480                1485

Gln Ala Thr Glu Asp Arg Leu Thr Ser Ala Lys Glu Leu Pro Tyr Phe
            1490                1495                1500

Glu Gly Asp Phe Trp Pro Asn Val Leu Glu Glu Ser Ile Lys Glu Leu
1505                1510                1515                1520

Glu Gln Glu Glu Glu Glu Arg Lys Arg Glu Glu Asn Thr Ser Asn Glu
            1525                1530                1535

Ser Thr Asp Val Thr Lys Gly Asp Ser Lys Asn Ala Lys Lys Lys Asn
            1540                1545                1550

Asn Lys Lys Thr Ser Lys Asn Lys Ser Ser Leu Ser Arg Gly Asn Lys
            1555                1560                1565

Lys Lys Pro Gly Met Pro Asn Val Ser Asn Asp Leu Ser Gln Lys Leu
            1570                1575                1580

Tyr Ala Thr Met Glu Lys His Lys Glu Val Phe Phe Val Ile Arg Leu
1585                1590                1595                1600

Ile Ala Gly Pro Ala Ala Asn Ser Leu Pro Pro Ile Val Asp Pro Asp
            1605                1610                1615

Pro Leu Ile Pro Cys Asp Leu Met Asp Gly Arg Asp Ala Phe Leu Thr
            1620                1625                1630

Leu Ala Arg Asp Lys His Leu Glu Phe Ser Ser Leu Arg Arg Ala Gln
            1635                1640                1645

Trp Ser Thr Met Cys Met Leu Val Glu Leu His Thr Gln Ser Gln Asp
            1650                1655                1660

Arg Phe Val Tyr Thr Cys Asn Glu Cys Lys His His Val Glu Thr Arg
1665                1670                1675                1680

Trp His Cys Thr Val Cys Glu Asp Tyr Asp Leu Cys Ile Thr Cys Tyr
            1685                1690                1695

Asn Thr Lys Asn His Asp His Lys Met Glu Lys Leu Gly Leu Gly Leu
            1700                1705                1710

Asp Asp Glu Ser Asn Asn Gln Gln Ala Ala Ala Thr Gln Ser Pro Gly
            1715                1720                1725

Asp Ser Arg Arg Leu Ser Ile Gln Arg Cys Ile Gln Ser Leu Val His
            1730                1735                1740

Ala Cys Gln Cys Arg Asn Ala Asn Cys Ser Leu Pro Ser Cys Gln Lys
1745                1750                1755                1760

Met Lys Arg Val Val Gln His Thr Lys Gly Cys Lys Arg Lys Thr Asn
            1765                1770                1775

Gly Gly Cys Pro Ile Cys Lys Gln Leu Ile Ala Leu Cys Cys Tyr His
            1780                1785                1790

Ala Lys His Cys Gln Glu Asn Lys Cys Pro Val Pro Phe Cys Leu Asn

-continued

```
                1795                1800                1805
Ile Lys Gln Lys Leu Arg Gln Gln Leu Gln His Arg Leu Gln Gln
            1810                1815                1820
Ala Gln Met Leu Arg Arg Arg Met Ala Ser Met Gln Arg Thr Gly Val
1825                1830                1835                1840
Val Gly Gln Gln Gln Gly Leu Pro Ser Pro Thr Pro Ala Thr Pro Thr
                1845                1850                1855
Thr Pro Thr Gly Gln Gln Pro Thr Thr Pro Gln Thr Pro Gln Pro Thr
            1860                1865                1870
Ser Gln Pro Gln Pro Thr Pro Pro Asn Ser Met Pro Pro Tyr Leu Pro
            1875                1880                1885
Arg Thr Gln Ala Ala Gly Pro Val Ser Gln Gly Lys Ala Ala Gly Gln
            1890                1895                1900
Val Thr Pro Pro Thr Pro Pro Gln Thr Ala Gln Pro Pro Leu Pro Gly
1905                1910                1915                1920
Pro Pro Pro Thr Ala Val Glu Met Ala Met Gln Ile Gln Arg Ala Ala
                1925                1930                1935
Glu Thr Gln Arg Gln Met Ala His Val Gln Ile Phe Gln Arg Pro Ile
            1940                1945                1950
Gln His Gln Met Pro Pro Met Thr Pro Met Ala Pro Met Gly Met Asn
            1955                1960                1965
Pro Pro Pro Met Thr Arg Gly Pro Ser Gly His Leu Glu Pro Gly Met
        1970                1975                1980
Gly Pro Thr Gly Met Gln Gln Pro Pro Trp Ser Gln Gly Gly Leu
1985                1990                1995                2000
Pro Gln Pro Gln Gln Leu Gln Ser Gly Met Pro Arg Pro Ala Met Met
            2005                2010                2015
Ser Val Ala Gln His Gly Gln Pro Leu Asn Met Ala Pro Gln Pro Gly
            2020                2025                2030
Leu Gly Gln Val Gly Ile Ser Pro Leu Lys Pro Gly Thr Val Ser Gln
            2035                2040                2045
Gln Ala Leu Gln Asn Leu Leu Arg Thr Leu Arg Ser Pro Ser Ser Pro
2050                2055                2060
Leu Gln Gln Gln Gln Val Leu Ser Ile Leu His Ala Asn Pro Gln Leu
2065                2070                2075                2080
Leu Ala Ala Phe Ile Lys Gln Arg Ala Ala Lys Tyr Ala Asn Ser Asn
            2085                2090                2095
Pro Gln Pro Ile Pro Gly Gln Pro Gly Met Pro Gln Gly Gln Pro Gly
            2100                2105                2110
Leu Gln Pro Pro Thr Met Pro Gly Gln Gln Gly Val His Ser Asn Pro
            2115                2120                2125
Ala Met Gln Asn Met Asn Pro Met Gln Ala Gly Val Gln Arg Ala Gly
            2130                2135                2140
Leu Pro Gln Gln Gln Pro Gln Gln Leu Gln Pro Pro Met Gly Gly
2145                2150                2155                2160
Met Ser Pro Gln Ala Gln Gln Met Asn Met Asn His Asn Thr Met Pro
            2165                2170                2175
Ser Gln Phe Arg Asp Ile Leu Arg Arg Gln Gln Met Met Gln Gln Gln
            2180                2185                2190
Gln Gln Gln Gly Ala Gly Pro Gly Ile Gly Pro Gly Met Ala Asn His
            2195                2200                2205
Asn Gln Phe Gln Gln Pro Gln Gly Val Gly Tyr Pro Pro Gln Pro Gln
            2210                2215                2220
```

-continued

Gln Arg Met Gln His His Met Gln Gln Met Gln Gln Gly Asn Met Gly
2225                2230                2235                2240

Gln Ile Gly Gln Leu Pro Gln Ala Leu Gly Ala Glu Ala Gly Ala Ser
                2245                2250                2255

Leu Gln Ala Tyr Gln Gln Arg Leu Leu Gln Gln Gln Met Gly Ser Pro
            2260                2265                2270

Val Gln Pro Asn Pro Met Ser Pro Gln Gln His Met Leu Pro Asn Gln
        2275                2280                2285

Ala Gln Ser Pro His Leu Gln Gly Gln Gln Ile Pro Asn Ser Leu Ser
    2290                2295                2300

Asn Gln Val Arg Ser Pro Gln Pro Val Pro Ser Pro Arg Pro Gln Ser
2305                2310                2315                2320

Gln Pro Pro His Ser Ser Pro Ser Pro Arg Met Gln Pro Gln Pro Ser
                2325                2330                2335

Pro His His Val Ser Pro Gln Thr Ser Ser Pro His Pro Gly Leu Val
            2340                2345                2350

Ala Ala Gln Ala Asn Pro Met Glu Gln Gly His Phe Ala Ser Pro Asp
        2355                2360                2365

Gln Asn Ser Met Leu Ser Gln Leu Ala Ser Asn Pro Gly Met Ala Asn
    2370                2375                2380

Leu His Gly Ala Ser Ala Thr Asp Leu Gly Leu Ser Thr Asp Asn Ser
2385                2390                2395                2400

Asp Leu Asn Ser Asn Leu Ser Gln Ser Thr Leu Asp Ile His
                2405                2410

<210> SEQ ID NO 3
<211> LENGTH: 781
<212> TYPE: PRT
<213> ORGANISM: Homo sapiens

<400> SEQUENCE: 3

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175

Gln Leu Ser Lys Lys Glu Ala Ser Arg His Ala Ile Met Arg Ser Pro

-continued

```
            180                 185                 190
Gln Met Val Ser Ala Ile Val Arg Thr Met Gln Asn Thr Asn Asp Val
            195                 200                 205
Glu Thr Ala Arg Cys Thr Ala Gly Thr Leu His Asn Leu Ser His His
210                 215                 220
Arg Glu Gly Leu Leu Ala Ile Phe Lys Ser Gly Ile Pro Ala Leu
225                 230                 235                 240
Val Lys Met Leu Gly Ser Pro Val Asp Ser Val Leu Phe Tyr Ala Ile
                    245                 250                 255
Thr Thr Leu His Asn Leu Leu His Gln Glu Gly Ala Lys Met Ala
                260                 265                 270
Val Arg Leu Ala Gly Gly Leu Gln Lys Met Val Ala Leu Leu Asn Lys
            275                 280                 285
Thr Asn Val Lys Phe Leu Ala Ile Thr Thr Asp Cys Leu Gln Ile Leu
290                 295                 300
Ala Tyr Gly Asn Gln Glu Ser Lys Leu Ile Ile Leu Ala Ser Gly Gly
305                 310                 315                 320
Pro Gln Ala Leu Val Asn Ile Met Arg Thr Tyr Thr Tyr Glu Lys Leu
                    325                 330                 335
Leu Trp Thr Thr Ser Arg Val Leu Lys Val Leu Ser Val Cys Ser Ser
                340                 345                 350
Asn Lys Pro Ala Ile Val Glu Ala Gly Gly Met Gln Ala Leu Gly Leu
            355                 360                 365
His Leu Thr Asp Pro Ser Gln Arg Leu Val Gln Asn Cys Leu Trp Thr
370                 375                 380
Leu Arg Asn Leu Ser Asp Ala Ala Thr Lys Gln Glu Gly Met Glu Gly
385                 390                 395                 400
Leu Leu Gly Thr Leu Val Gln Leu Leu Gly Ser Asp Asp Ile Asn Val
                    405                 410                 415
Val Thr Cys Ala Ala Gly Ile Leu Ser Asn Leu Thr Cys Asn Asn Tyr
                420                 425                 430
Lys Asn Lys Met Met Val Cys Gln Val Gly Gly Ile Glu Ala Leu Val
            435                 440                 445
Arg Thr Val Leu Arg Ala Gly Asp Arg Glu Asp Ile Thr Glu Pro Ala
450                 455                 460
Ile Cys Ala Leu Arg His Leu Thr Ser Arg His Gln Glu Ala Glu Met
465                 470                 475                 480
Ala Gln Asn Ala Val Arg Leu His Tyr Gly Leu Pro Val Val Val Lys
                    485                 490                 495
Leu Leu His Pro Pro Ser His Trp Pro Leu Ile Lys Ala Thr Val Gly
                500                 505                 510
Leu Ile Arg Asn Leu Ala Leu Cys Pro Ala Asn His Ala Pro Leu Arg
            515                 520                 525
Glu Gln Gly Ala Ile Pro Arg Leu Val Gln Leu Leu Val Arg Ala His
            530                 535                 540
Gln Asp Thr Gln Arg Arg Thr Ser Met Gly Gly Thr Gln Gln Gln Phe
545                 550                 555                 560
Val Glu Gly Val Arg Met Glu Glu Ile Val Glu Gly Cys Thr Gly Ala
                    565                 570                 575
Leu His Ile Leu Ala Arg Asp Val His Asn Arg Ile Val Ile Arg Gly
                580                 585                 590
Leu Asn Thr Ile Pro Leu Phe Val Gln Leu Leu Tyr Ser Pro Ile Glu
            595                 600                 605
```

-continued

```
Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
    690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
    770                 775                 780

<210> SEQ ID NO 4
<211> LENGTH: 745
<212> TYPE: PRT
<213> ORGANISM: Homo sapiens

<400> SEQUENCE: 4

Met Glu Val Met Asn Leu Met Glu Gln Pro Ile Lys Val Thr Glu Trp
1               5                   10                  15

Gln Gln Thr Tyr Thr Tyr Asp Ser Gly Ile His Ser Gly Ala Asn Thr
            20                  25                  30

Cys Val Pro Ser Val Ser Ser Lys Gly Ile Met Glu Glu Asp Glu Ala
        35                  40                  45

Cys Gly Arg Gln Tyr Thr Leu Lys Lys Thr Thr Thr Tyr Thr Gln Gly
    50                  55                  60

Val Pro Pro Ser Gln Gly Asp Leu Glu Tyr Gln Met Ser Thr Thr Ala
65                  70                  75                  80

Arg Ala Lys Arg Val Arg Glu Ala Met Cys Pro Gly Val Ser Gly Glu
                85                  90                  95

Asp Ser Ser Leu Leu Leu Ala Thr Gln Val Glu Gly Gln Ala Thr Asn
            100                 105                 110

Leu Gln Arg Leu Ala Glu Pro Ser Gln Leu Leu Lys Ser Ala Ile Val
        115                 120                 125

His Leu Ile Asn Tyr Gln Asp Asp Ala Glu Leu Ala Thr Arg Ala Leu
    130                 135                 140

Pro Glu Leu Thr Lys Leu Leu Asn Asp Glu Asp Pro Val Val Val Thr
145                 150                 155                 160

Lys Ala Ala Met Ile Val Asn Gln Leu Ser Lys Lys Glu Ala Ser Arg
                165                 170                 175

Arg Ala Leu Met Gly Ser Pro Gln Leu Val Ala Ala Val Val Arg Thr
            180                 185                 190

Met Gln Asn Thr Ser Asp Leu Asp Thr Ala Arg Cys Thr Thr Ser Ile
```

```
                195                 200                 205
Leu His Asn Leu Ser His His Arg Glu Gly Leu Leu Ala Ile Phe Lys
    210                 215                 220

Ser Gly Gly Ile Pro Ala Leu Val Arg Met Leu Ser Ser Pro Val Glu
225                 230                 235                 240

Ser Val Leu Phe Tyr Ala Ile Thr Thr Leu His Asn Leu Leu Leu Tyr
                245                 250                 255

Gln Glu Gly Ala Lys Met Ala Val Arg Leu Ala Asp Gly Leu Gln Lys
            260                 265                 270

Met Val Pro Leu Leu Asn Lys Asn Asn Pro Lys Phe Leu Ala Ile Thr
        275                 280                 285

Thr Asp Cys Leu Gln Leu Leu Ala Tyr Gly Asn Gln Glu Ser Lys Leu
    290                 295                 300

Ile Ile Leu Ala Asn Gly Gly Pro Gln Ala Leu Val Gln Ile Met Arg
305                 310                 315                 320

Asn Tyr Ser Tyr Glu Lys Leu Leu Trp Thr Thr Ser Arg Val Leu Lys
                325                 330                 335

Val Leu Ser Val Cys Pro Ser Asn Lys Pro Ala Ile Val Glu Ala Gly
            340                 345                 350

Gly Met Gln Ala Leu Gly Lys His Leu Thr Ser Asn Ser Pro Arg Leu
        355                 360                 365

Val Gln Asn Cys Leu Trp Thr Leu Arg Asn Leu Ser Asp Val Ala Thr
    370                 375                 380

Lys Gln Glu Gly Leu Glu Ser Val Leu Lys Ile Leu Val Asn Gln Leu
385                 390                 395                 400

Ser Val Asp Asp Val Asn Val Leu Thr Cys Ala Thr Gly Thr Leu Ser
                405                 410                 415

Asn Leu Thr Cys Asn Asn Ser Lys Asn Lys Thr Leu Val Thr Gln Asn
            420                 425                 430

Ser Gly Val Glu Ala Leu Ile His Ala Ile Leu Arg Ala Gly Asp Lys
        435                 440                 445

Asp Asp Ile Thr Glu Pro Ala Val Cys Ala Leu Arg His Leu Thr Ser
    450                 455                 460

Arg His Pro Glu Ala Glu Met Ala Gln Asn Ser Val Arg Leu Asn Tyr
465                 470                 475                 480

Gly Ile Pro Ala Ile Val Lys Leu Leu Asn Gln Pro Asn Gln Trp Pro
                485                 490                 495

Leu Val Lys Ala Thr Ile Gly Leu Ile Arg Asn Leu Ala Leu Cys Pro
            500                 505                 510

Ala Asn His Ala Pro Leu Gln Glu Ala Ala Val Ile Pro Arg Leu Val
        515                 520                 525

Gln Leu Leu Val Lys Ala His Gln Asp Ala Gln Arg His Val Ala Ala
    530                 535                 540

Gly Thr Gln Gln Pro Tyr Thr Asp Gly Val Arg Met Glu Glu Ile Val
545                 550                 555                 560

Glu Gly Cys Thr Gly Ala Leu His Ile Leu Ala Arg Asp Pro Met Asn
                565                 570                 575

Arg Met Glu Ile Phe Arg Leu Asn Thr Ile Pro Leu Phe Val Gln Leu
            580                 585                 590

Leu Tyr Ser Ser Val Glu Asn Ile Gln Arg Val Ala Ala Gly Val Leu
        595                 600                 605

Cys Glu Leu Ala Gln Asp Lys Glu Ala Ala Asp Ala Ile Asp Ala Glu
    610                 615                 620
```

```
Gly Ala Ser Ala Pro Leu Met Glu Leu Leu His Ser Arg Asn Glu Gly
625                 630             635                 640

Thr Ala Thr Tyr Ala Ala Ala Val Leu Phe Arg Ile Ser Glu Asp Lys
                645             650                 655

Asn Pro Asp Tyr Arg Lys Arg Val Ser Val Glu Leu Thr Asn Ser Leu
            660             665             670

Phe Lys His Asp Pro Ala Ala Trp Glu Ala Ala Gln Ser Met Ile Pro
        675             680                 685

Ile Asn Glu Pro Tyr Gly Asp Asp Met Asp Ala Thr Tyr Arg Pro Met
    690             695             700

Tyr Ser Ser Asp Val Pro Leu Asp Pro Leu Glu Met His Met Asp Met
705             710             715                 720

Asp Gly Asp Tyr Pro Ile Asp Thr Tyr Ser Asp Gly Leu Arg Pro Pro
            725             730             735

Tyr Pro Thr Ala Asp His Met Leu Ala
            740         745
```